(12) United States Patent
 Livne et al.

(10) Patent No.: US 9,918,708 B2
(45) Date of Patent: Mar. 20, 2018

(54) TISSUE RETRACTOR

(71) Applicant: LapSpace Medical Ltd., Misgav Business park (IL)

(72) Inventors: Assaf Livne, Tel-Aviv (IL); Gilad Lavi, Rishon-LeZion (IL); Hien Nguyen, Baltimore, MD (US)

(73) Assignee: LapSpace Medical Ltd., Misgav Business park (IL)

( * ) Notice: Subject to any disclaimer, the term of this patent is extended or adjusted under 35 U.S.C. 154(b) by 0 days.

(21) Appl. No.: 14/387,241

(22) PCT Filed: Mar. 21, 2013

(86) PCT No.: PCT/IL2013/050280
§ 371 (c)(1),
(2) Date: Sep. 23, 2014

(87) PCT Pub. No.: WO2013/144959
PCT Pub. Date: Oct. 3, 2013

(65) Prior Publication Data
US 2015/0057501 A1    Feb. 26, 2015

Related U.S. Application Data

(60) Provisional application No. 61/706,193, filed on Sep. 27, 2012, provisional application No. 61/617,182, filed on Mar. 29, 2012.

(51) Int. Cl.
| | |
|---|---|
| *A61B 1/00* | (2006.01) |
| *A61B 17/02* | (2006.01) |
| *A61B 17/34* | (2006.01) |
| *A61B 17/00* | (2006.01) |

(52) U.S. Cl.
CPC ...... *A61B 17/0218* (2013.01); *A61B 17/3423* (2013.01); *A61B 2017/00314* (2013.01);
(Continued)

(58) Field of Classification Search
CPC ........... A61B 2017/00323; A61B 2017/00557; A61B 2017/0212
See application file for complete search history.

(56) References Cited

U.S. PATENT DOCUMENTS

| | | | |
|---|---|---|---|
| 3,196,865 A * | 7/1965 | Rose | A61B 17/02 600/226 |
| 3,863,639 A | 2/1975 | Kleaveland | |

(Continued)

FOREIGN PATENT DOCUMENTS

| | | |
|---|---|---|
| CN | 101873832 | 10/2010 |
| CN | 201701244 | 1/2011 |

(Continued)

OTHER PUBLICATIONS

Notificaiton of Reasons for Refusal dated Nov. 17, 2015 From the Japanese Patent Office Re. Applciation No. 2013-547730 and Its Translation Into English.
(Continued)

*Primary Examiner* — Jan Christopher Merene
*Assistant Examiner* — Atiya Mahmud

(57) ABSTRACT

A tissue retractor device is provided. The tissue retractor device includes a handle attached to an inflatable rake-shaped tissue retractor head.

16 Claims, 28 Drawing Sheets

(52) U.S. Cl.
CPC .............. *A61B 2017/00323* (2013.01); *A61B 2017/00535* (2013.01); *A61B 2017/00557* (2013.01); *A61B 2017/0212* (2013.01); *A61B 2017/0225* (2013.01)

(56) References Cited

U.S. PATENT DOCUMENTS

| | | | |
|---|---|---|---|
| 5,163,949 A | 11/1992 | Bonutti | |
| 5,195,507 A * | 3/1993 | Bilweis | A61B 1/00082 600/204 |
| 5,280,282 A * | 1/1994 | Nagafusa | B63H 21/213 180/287 |
| 5,308,327 A * | 5/1994 | Heaven | A61B 17/00234 604/103.09 |
| 5,318,586 A | 6/1994 | Ereren | |
| 5,359,995 A | 11/1994 | Sewell, Jr. | |
| 5,400,773 A | 3/1995 | Zhu et al. | |
| 5,520,609 A | 5/1996 | Moll et al. | |
| 5,540,711 A | 7/1996 | Kieturakis et al. | |
| 5,588,951 A | 12/1996 | Zhu et al. | |
| 5,613,937 A | 3/1997 | Garrison et al. | |
| 5,649,902 A | 7/1997 | Yoon | |
| 5,772,680 A | 6/1998 | Kieturakis et al. | |
| 5,836,871 A | 11/1998 | Wallace et al. | |
| 5,865,728 A | 2/1999 | Moll et al. | |
| 5,865,802 A | 2/1999 | Yoon et al. | |
| 5,895,352 A * | 4/1999 | Kleiner | A61B 17/02 600/206 |
| 5,992,680 A | 11/1999 | Smith | |
| 6,032,671 A | 3/2000 | Mollenauer et al. | |
| 6,036,641 A | 3/2000 | Taylor et al. | |
| 6,146,401 A | 11/2000 | Yoon et al. | |
| 6,149,583 A * | 11/2000 | Vierra | A61B 17/0469 600/204 |
| 7,758,500 B2 | 7/2010 | Boyd et al. | |
| 2003/0225432 A1 | 12/2003 | Baptiste et al. | |
| 2004/0097792 A1 | 5/2004 | Moll et al. | |
| 2004/0127931 A1 | 7/2004 | Kincaid et al. | |
| 2005/0090717 A1 | 4/2005 | Bonadio et al. | |
| 2005/0203344 A1 | 9/2005 | Orban, III et al. | |
| 2005/0245960 A1 | 11/2005 | Grundeman | |
| 2008/0188868 A1 | 8/2008 | Weitzner et al. | |
| 2008/0300618 A1 | 12/2008 | Gertner | |
| 2009/0137984 A1 | 5/2009 | Minnelli | |
| 2009/0287046 A1 | 11/2009 | Yamatani | |
| 2009/0312807 A1 | 12/2009 | Boudreault et al. | |
| 2010/0016674 A1 | 1/2010 | Mills | |
| 2010/0069947 A1 | 3/2010 | Sholev | |
| 2010/0168523 A1 | 7/2010 | Durcharme | |
| 2010/0286485 A1* | 11/2010 | Valentini | A61B 1/32 600/224 |
| 2011/0040152 A1 | 2/2011 | Kim et al. | |
| 2011/0054408 A1 | 3/2011 | Wei et al. | |
| 2011/0190591 A1* | 8/2011 | Palmer | A61B 1/32 600/226 |
| 2011/0190781 A1 | 8/2011 | Collier et al. | |
| 2012/0238825 A1 | 9/2012 | Smith | |
| 2013/0131710 A1 | 5/2013 | Carmeli et al. | |
| 2013/0178709 A1 | 7/2013 | Suh et al. | |
| 2015/0245828 A1 | 9/2015 | Harari et al. | |
| 2016/0007985 A1 | 1/2016 | Jin et al. | |
| 2016/0100857 A1 | 4/2016 | Wachli et al. | |
| 2016/0113717 A1 | 4/2016 | Csernatoni | |
| 2016/0270775 A1 | 9/2016 | Nguyen | |

FOREIGN PATENT DOCUMENTS

| | | |
|---|---|---|
| CN | 102028511 | 4/2011 |
| EP | 0490714 | 6/1992 |
| FR | 2726993 | 5/1996 |
| FR | 2737401 | 2/1997 |
| FR | 2726993 | 5/1998 |
| JP | 06-507810 | 9/1994 |
| JP | 10-511589 | 11/1998 |
| JP | 2003-164459 | 6/2003 |
| WO | WO 92/21291 | 12/1992 |
| WO | WO 92/21293 | 12/1992 |
| WO | WO 93/10850 | 6/1993 |
| WO | WO 94/16630 | 8/1994 |
| WO | WO 96/20749 | 7/1996 |
| WO | WO 97/32514 | 9/1997 |
| WO | WO 99/20321 | 4/1999 |
| WO | WO 02/28331 | 4/2002 |
| WO | WO 2005/102185 | 11/2005 |
| WO | WO 2009/144729 | 12/2009 |
| WO | WO 2010/042844 | 4/2010 |
| WO | WO 2010/078315 | 7/2010 |
| WO | WO 2012/094364 | 7/2012 |
| WO | WO 2013/144959 | 10/2013 |

OTHER PUBLICATIONS

International Preliminary Report on Patentability dated Oct. 9, 2014 From the International Bureau of WIPO Re. Application No. PCT/IL2013/050280.

International Search Report and the Written Opinion dated Sep. 6, 2013 From the International Searching Authority Re. Application No. PCT/IL2013/050280.

Invitation to Pay Additional Fees dated Jul. 16, 2013 From the International Searching Authority Re. Application No. PCT/IL2013/050280.

International Preliminary Report on Patentability dated Oct. 9, 2014 From the International Bureau of WIPO Re. Application No. PCT/US2012/020138.

International Search Report and the Written Opinion dated Jun. 28, 2012 From the International Searching Authority Re. Application No. PCT/US2012/020138.

Official Action dated Mar. 30, 2015 From the US Patent and Trademark Office Re. U.S. Appl. No. 13/978,200.

Notification of Office Action and Search Report dated Jul. 27, 2015 From the State Intellectual Property Office of the People's Republic of China Re. Application No. 201380027547.4 and Description of Office Action in English.

Supplementary European Search Report and the European Search Opinion dated Jun. 25, 2015 From the European Patent Office Re. Application No. 12732225.3.

Notification of Office Action dated Jan. 7, 2015 From the State Intellectual Property Office of the People's Republic of China Re. Application No. 201280004574.5 and Its Summary in English.

Notification of Office Action dated Sep. 30, 2015 From the State Intellectual Property Office of the People's Republic of China Re. Application No. 201280004574.5 and Its Summary in English.

Supplementary European Search Report and the European Search Opinion dated Nov. 12, 2015 From the European Patent Office Re. Application No. 13767950.2.

Reasons for Rejection dated Apr. 5, 2016 From the State Intellectual Property Office of the People's Republic of China Re. Application No. 201380027547.4 and Its Translation Into English.

Communication Pursuant to Article 94(3) EPC dated Mar. 10, 2017 From the European Patent Office Re. Application No. 12732225.3. (9 Pages).

Restriction Official Action dated Sep. 2, 2016 From the US Patent and Trademark Office Re. U.S. Appl. No. 14/635,073.

Communication Pursuant to Article 94(3) EPC dated Jan. 27, 2017 From the European Patent Office Re. Application No. 13767950.2. (4 Pages).

Official Action dated Dec. 29, 2016 From the US Patent and Trademark Office Re. U.S. Appl. No. 14/635,073. (40 pages).

Notice of Rejection Decision dated Jun. 23, 2017 From the State Intellectual Property Office of the People's Republic of China Re. Application No. 201380027547.4 and Its Summary in English. (9 Pages).

Notification of Office Action and Search Report dated Oct. 19, 2016 From the State Intellectual Property Office of the People's Republic of China Re. Application No. 201380027547.4. (6 Pages).

(56) References Cited

OTHER PUBLICATIONS

Translation of Notification of Office Action dated Oct. 19, 2016 From the State Intellectual Property Office of the People's Republic of China Re. Application No. 201380027547.4. (2 Pages).
Communication Pursuant to Article 94(3) EPC Dated Oct. 27, 2017 From the European Patent Office Re. Application No. 13767950.2. (6 Pages).

* cited by examiner

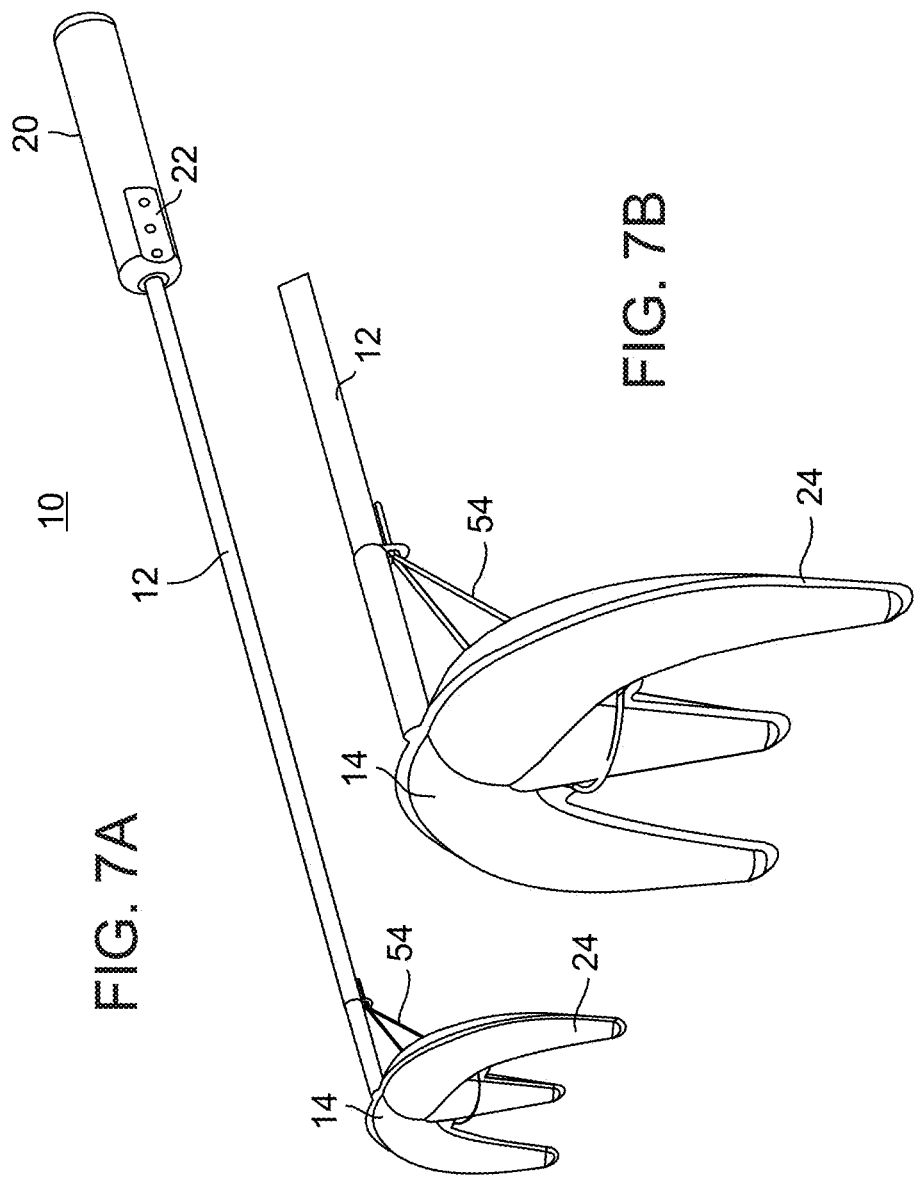

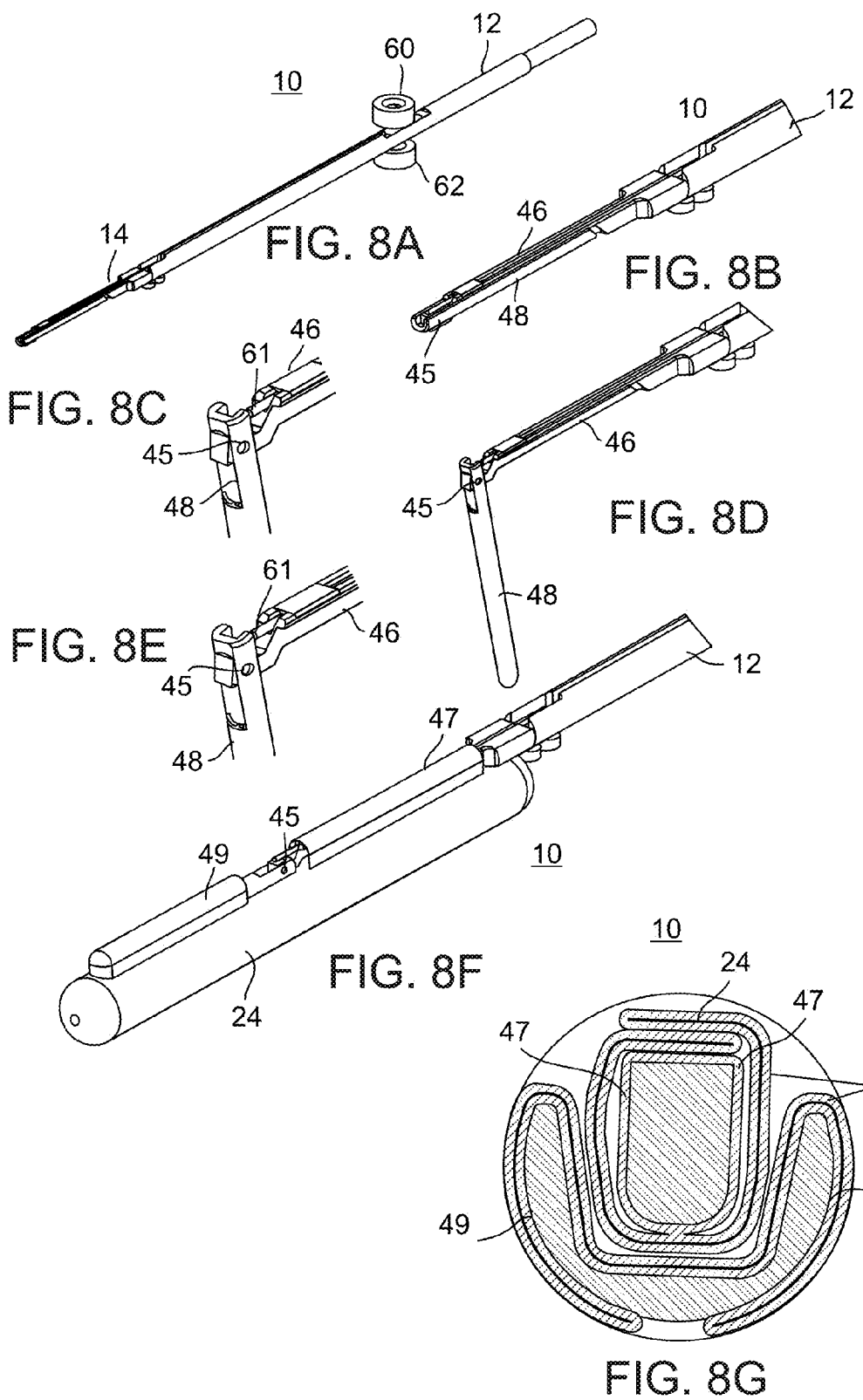

TISSUE RETRACTOR

RELATED APPLICATIONS

This application is a National Phase of PCT Patent Application No. PCT/IL2013/050280 having International filing date of Mar. 21, 2013, which claims the benefit of priority under 35 USC § 119(e) of U.S. Provisional Patent Application No. 61/617,182 filed on Mar. 29, 2012 and U.S. Provisional Patent Application No. 61/706,193 filed on Sep. 27, 2012. The contents of the above applications are all incorporated by reference as if fully set forth herein in their entirety.

FIELD AND BACKGROUND OF THE INVENTION

The present invention relates to a tissue retractor and, more particularly, to a tissue retractor that includes an inflatable tissue retractor head. The present invention also relates to a passive diffusion system which can be integrated into, or used along with the retractor of the present invention.

Minimally invasive surgery (MIS) is a surgical technique in which a body cavity (e.g. abdominal cavity) is accessed via several small incisions as opposed to the large incision access used in open surgery.

Surgical tools are inserted into the body cavity through ports positioned within the small incisions with the actuating handles of the surgical tools positioned outside the body. The surgeon manipulates the surgical tool via the handle while viewing the operative field on a video feed provided by a camera and a light source mounted on a rod inserted through one of the ports.

During minimally invasive surgery, the surgeon is required to expose and handle delicate tissues deep within the body cavities. This requires creation and maintenance of a surgical workspace large enough to enable the surgeon to view and work within the treatment area without damaging surrounding tissues.

To provide the surgeon with a good view of the operative filed, the body cavity is usually insufflated with carbon dioxide gas and organs that obstruct the field of view of the camera and block access to the treatment area are retracted using a tissue retractor.

Tissue retractors are generally inserted into the body cavity in a collapsed conformation through an additional port, and are then expanded within the body and either held by an assistant or fixed to an object such as the operating table.

Tissue retractors known in the art typically utilize mechanically deployable arms/fingers (the Endo Retract™ by BioMedicon), baskets (A-Lap by EZSurgical) or hooks (Virtual Ports) which can be used to sweep and/or move tissue organs out of the treatment area. Inflatable retractors are also known in the art (e.g. Extrahand™ Balloon Retractor by BioMedicon), however due to their simple paddle-like configuration such retractors are more suitable for containing tissue than retracting it.

Although prior art mechanical retractors can be effectively used to retract and contain tissue, use thereof typically carries a tradeoff between creation and maintenance of an adequate surgical workspace and retractor-induced damage to surrounding tissues.

There is thus a need for a tissue retractor that can be used to safely and effectively retract and contain tissue thus providing a surgical workspace while minimizing damage to surrounding tissues.

SUMMARY OF THE INVENTION

According to one aspect of the present invention there is provided tissue retractor device comprising a handle attached to an inflatable tissue retractor head being configured such that when inflated with a fluid, the tissue retractor head includes at least one extension sized and configured for enabling the tissue retractor head to hook over tissue thereby enabling retraction and/or containment of the tissue within a body cavity.

According to further features in preferred embodiments of the invention described below, the tissue retractor head is deliverable through a laparoscopic port (e.g. a 5-12 mm trocar port) when in a deflated state.

According to still further features in the described preferred embodiments the at least one extension is configured as a prong or hook.

According to still further features in the described preferred embodiments the tissue retractor head is sized and configured for hooking over an intestine when inflated with the fluid.

According to still further features in the described preferred embodiments a shape of the tissue retractor head and/or the extension is determined by a degree of inflation thereof.

According to still further features in the described preferred embodiments the extension is shaped as a prong following a first inflation (of, for example a first inflatable compartment) and as a hook following further inflation (of, for example, a second inflatable compartment).

According to still further features in the described preferred embodiments the tissue retractor head is composed of a polymer, preferably a non-compliant polymer. Such a polymer is preferably configured as two opposing flat sheets which are glued/welded into a 2-D structure which when inflated assumes a 3-D structure (balloon-like).

According to still further features in the described preferred embodiments the polymer is selected from the group consisting of polyurethane, silicone, and polyethylene.

According to still further features in the described preferred embodiments the tissue retractor head includes mechanical struts. In other embodiments the tissue retractor head does not include struts and assumes a rigid structure by virtue of inflation only.

According to still further features in the described preferred embodiments the mechanical struts are positioned within or upon the inflatable structure.

According to still further features in the described preferred embodiments the mechanical struts determine a shape of the tissue retractor head when inflated or limit a final inflation volume thereof.

According to still further features in the described preferred embodiments the mechanical struts are deployed by inflation of the extension.

According to still further features in the described preferred embodiments the tissue retractor head is configured as a rake, a claw, or a hook.

According to still further features in the described preferred embodiments the device is sized and configured for use in laparoscopic surgery and video assisted thoracic surgery.

According to still further features in the described preferred embodiments the at least one extension can be inflated (e.g. following engagement of organ) to grasp the organ.

According to still further features in the described preferred embodiments a first inflation of the at least one extension forms a hook and a second inflation reduces an open aperture of the hook.

According to still further features in the described preferred embodiments the tissue retractor head includes a plurality of individually inflatable compartments.

According to another aspect of the present invention there is provided a method of retracting a tissue organ comprising: (a) positioning a tissue retractor device including a handle attached to an inflatable tissue retractor head within a body cavity; (b) partially inflating the tissue retractor head in a position over the tissue organ; (c) further inflating the tissue retractor head to hook over the tissue organ; and (d) using the tissue retractor device to retract and optionally trap the tissue organ.

According to still further features in the described preferred embodiments the method further comprises additionally inflating the tissue retractor head following (c) to thereby grasp the tissue organ.

According to still further features in the described preferred embodiments the method further comprises (e), partially deflating the tissue retractor head.

According to still further features in the described preferred embodiments the tissue retractor head includes a plurality of separately inflatable compartments such that (b) inflates a first inflatable compartment and (c) inflates a second inflatable compartment.

According to still further features in the described preferred embodiments the method further comprises mechanically fixating the tissue retractor head in a predetermined position following (c), by for example locking a position and/or angulation of the mechanical struts.

According to another aspect of the present invention there is provided a tissue retractor device comprising an inflatable tissue retractor head being configured such that when inflated with a fluid, the tissue retractor head forms a flat configuration which includes a plurality of finger-like extensions; and (b) a handle including a mechanism for angling a portion of the tissue retractor head which includes the extensions with respect to the handle during or following inflation of the tissue retractor head.

According to still further features in the described preferred embodiments the mechanism for angling the portion of the tissue retractor head is a movable strap attached to at least one of the extensions.

According to still further features in the described preferred embodiments the handle includes a fluid conduit for allowing fluids to diffuse from an opening at the tissue retractor head to the handle.

According to another aspect of the present invention there is provided a system for facilitating diffusion of fluids out of a body cavity, the system comprising: (a) a cannula having a fluid conduit; and (b) a reservoir fluidly connected to a proximal end of the cannula; the cannula being configured for positioning across a tissue wall defining a body cavity and being capable of supporting passive diffusion of fluids out of the body cavity and into the reservoir.

According to still further features in the described preferred embodiments the reservoir is a pliable container.

According to still further features in the described preferred embodiments the reservoir is a rigid container including a vent valve for releasing pressure buildup within the container.

The present invention successfully addresses the shortcomings of the presently known configurations by providing a tissue retractor device capable of engaging, retracting and containing tissue during a minimally invasive procedure.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 7A-I illustrate a rake-like device including an inflatable tissue retractor head attached to the handle via a wire/strap which determines an angulation of the tissue support head with respect to the handle.

FIGS. 8A-H illustrate the components and various deployment states of the embodiment of the present device shown in FIGS. 5A-B.

DESCRIPTION OF THE PREFERRED EMBODIMENTS

Figure 1A:
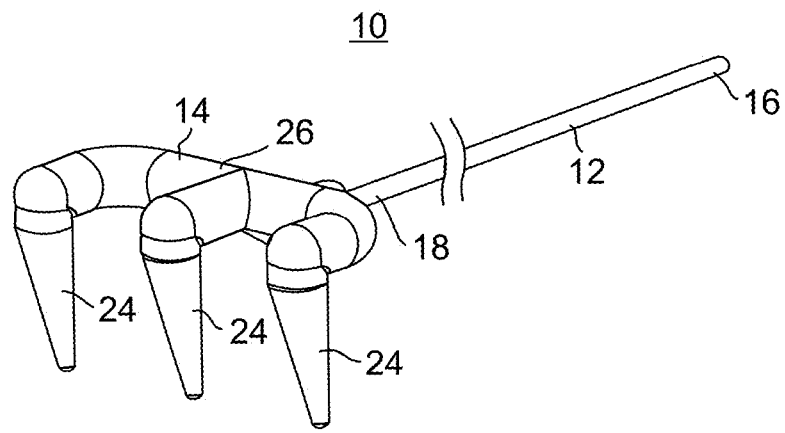
FIGS. 1A-B illustrate a rake embodiment of the present device in isometric FIG. 1A) and side (FIG. 1B) views.

The present invention is of a tissue retractor which can be used in a laparoscopic surgical procedure to grasp, move and contain tissue organs. Specifically, the present invention can be used to atraumatically grasp and move tissue organs within a body cavity through a laparoscopic port and effectively contain such organs during a laparoscopic procedure.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Although laparoscopic retractors capable of grasping, moving and containing tissue are known in the art, current designs oftentimes present a tradeoff between grasping and moving, and containment; i.e. devices designed for grasping and moving are oftentimes less effective in containing the retracted organ. In addition, due to their rigid design and relatively hard tissue-contacting surfaces, presently used retractors apply excessive forces on tissues of retracted organs especially when utilized over extended time periods. Studies have shown that such forces can lead to tissue ischemia and severe organ injury [see, for example, Pasenau et. al., Surgical Laparoscopy, Endoscopy, and Percutaneous Techniques. 10(3):178-181 2000].

While reducing the present invention to practice, the present inventors have devised a tissue retractor that can be effectively used for grasping and moving tissue as well as containing it while minimizing trauma to the organ and surrounding tissue.

As is further described hereinunder, the present device includes an inflatable tissue retraction head (e.g. non-compliant balloon) which is configured for selectively engaging, grasping and containing tissue organs. Such selective modes of operation are controlled by the degree of deployment of the tissue retractor head which is in turn controlled by inflation and/or by mechanical elements.

The tissue retractor of the present invention provides several advantages:

(i) it enables top access to tissue, i.e. the organ is engaged from the top (organ surface proximal to access port) by hooking the retractor head over the organ, this negates the need to 'dig' under the organ and possibly damage underlying invisible tissues;

(ii) the tissue retractor head is inflatable and as such tissue engagement is via a relatively soft and elastic interface thus reducing damage to contacted tissues as well as surrounding tissues;

(iii) it enables secure containment of tissue thus reducing tissue movement against the retractor which can result in tissue erosion;

(iv) use of inflated element reduces the level of complexity (increased reliability)—balloon acts as actuator (expands to a preset shape under pressure);

(v) self-fixation of retractor head negates the need for holding the device during retraction.

Thus, according to one aspect of the present invention there is provided a tissue retractor device for in surgery, preferably minimally invasive surgery.

As used herein, the phrase "minimally invasive surgery" (also "endoscopic surgery") refers to a surgical procedure in which the surgical workspace is not directly viewed or accessed by a surgeon. Laparoscopic surgery includes operations within the abdominal or pelvic cavities, whereas thoracoscopic surgery includes operations within the thoracic or chest cavity.

The device of the present invention includes a handle which is attached to an inflatable tissue retractor head.

The handle can have any diameter and length suitable for minimally invasive surgery. Depending on the type of surgery, the configuration of the tissue retractor head and the size of access port used (inner diameter of cannula or trocar port), the handle can be anywhere from 10 cm in length and 5 mm in diameter. The distal end of the handle is mechanically connected to the tissue retractor head via an immovable or hinged connection. Since the tissue retractor head is at least partially deployable via inflation, fluid conduits running through the handle connect the tissue retractor head to a fluid source which can be situated within the handle or external to the device (in which case fluid ports are provided in the proximal end of the handle). The proximal side of the handle provides an interface with the surgeon, and thus includes controls over deployment and positioning of the tissue retractor head.

A more detailed description of the device handle is provided hereinbelow with respect to specific device configurations.

The inflatable tissue retractor head positioned at the distal end of the handle is configured such that when inflated with a fluid (e.g. Air, $CO_2$ or Nitrogen gas, water, saline), it includes at least one extension which is sized and configured for enabling the tissue retractor head to hook over a tissue of, for example, an organ such as an intestine, a liver, a spleen, a lung, a uterus, a stomach, a kidney, a blood vessel such as an artery and connective tissue, fascia and the like.

The tissue retractor head can be configured as one or more interconnected extensions, or as one or more extensions projecting from a retractor head body. The extension or extensions typically angle away from the longitudinal plane of the handle by 20-60 degrees or by 20-60 degrees from the retractor head body depending on the shape and size of the extension and purpose of the device. Specific examples of retractor head configurations are described in detail hereinbelow.

As used herein, the phrase "hook over" refers to the ability of the tissue retractor head to contact more than one side of a tissue when applied from the top thereof (i.e. the surface pointed in the direction of the surgical access incision). For example, in the case of an intestine, the tissue retractor head contacts more than 90 degrees of the organ circumference, preferably more than 180 degrees of the organ circumference, most preferably more than 270 degrees of the organ circumference when hooked over the organ.

As is further described herein, such an extension can be of any shape or size suitable for hooking over and optionally grasping the organ. Examples include, include a prong, a hook, a claw and the like.

The functional shape of the deployed extension is dictated by one or more mechanisms. In the simplest configuration of the present device, the shape of the extension is largely controlled by inflation, i.e. the volume of inflation dictates the extent of deployment of the extension and its shape. In such cases, the extension is formed from a non-compliant balloon of a predetermined inflatable shape and volume. For example, inflation of the tissue retractor head to a first predetermined volume can form an extension in a shape of a prong, while further inflation of the prong can form a hook. The transformation of the prong to a hook can take place by simply filling the same inflatable compartment with more fluid or by filling a second compartment which extends the prong into a hook. Alternatively, the shape and size of the extension can be governed by mechanical elements included within, or attached to, the inflatable tissue retractor head. For example, transformation between a prong and hook can take place by retracting a mechanical limiter off of a prong and further inflating the prong to form a hook. Further description of controlled and stepwise deployment of extensions is provided hereinbelow.

Such controlled, stepwise deployment of the extension provides several advantages in grasping, moving and containing tissue. For example, partial deployment of a prong can be used for sweeping/raking tissue while full deployment as a hook enables grasping/lifting and moving of tissue. Conversely, deflation of a hook extension down to a prong can be used to more easily contain tissue following retraction.

As is further described herein, the present device can be used to retract and contain tissue in any minimally invasive procedure.

The present device can be configured in numerous sizes and shapes depending on the tissue targeted for retraction and the body cavity accessed. For example, when used in a laparoscopic procedure in an abdominal cavity, the present device can be configured with the following features:

(i) insertion in a deflated and packaged form through a 5-12 mm trocar port;

(ii) deployment within the abdominal cavity to a pre-set shape which can be controlled via inflation and/or mechanical elements;

(iii) penetration into the intestinal mass to enable hooking/grasping of intestinal sections;

(iv) pushing/pulling aside and containing the intestinal mass to expose a target tissue;

(v) fixation and stabilization in order to maintain the retracted tissue contained during the procedure;

(vi) simple and quick release (and recapture if necessary) of intestinal tissue;

(vii) simple and quick contraction (deflation) of the tissue retractor head and easy removal of the device from the body.

The following provides several exemplary configurations of the present device. Referring now to the drawings, FIGS. 1-9 illustrate various embodiments of the present device which is referred to herein as device 10.

Figure 1B:
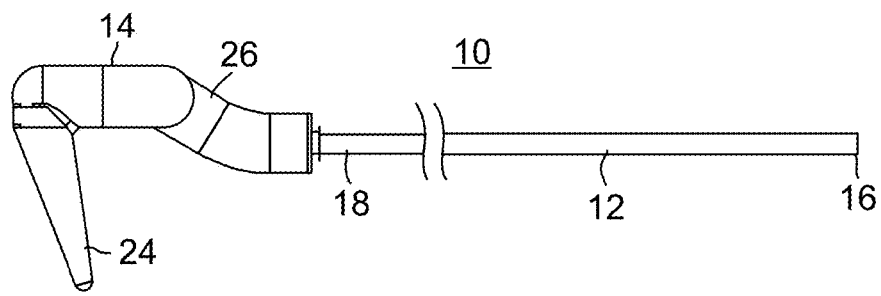

As is shown in FIGS. 1a-b device 10 includes a handle 12 (which includes a user engagement portion and a shaft) attached to a tissue retractor head 14. Handle 12 is configured as an elongated shaft about 10-50 cm in length and 3-15 mm in diameter. Handle 12 can be fabricated from an alloy or polymer using techniques well known in the art. Handle 12 is preferably hollow and/or includes fluid conduits that extend from a proximal end 16 of handle 12 to a distal end 18 thereof. The fluid conduits (not shown) enable inflation of tissue retractor head 14 with a fluid maintained under pressure in proximal side 16 of handle 12 or an external reservoir or pumping element (not shown).

Handle 12 is preferably rigid but can include joints (e.g. hinges or swivel joints) for articulation of one portion of handle 12 with respect to another. Such joints can be positioned close to distal end 18 or at a middle portion of handle 12. Articulation around the joint can be controlled from proximal end 16 of handle 12 via a set of cables, geared transmission, threaded rods or axial plungers running within a lumen of handle 12.

Figure 2:
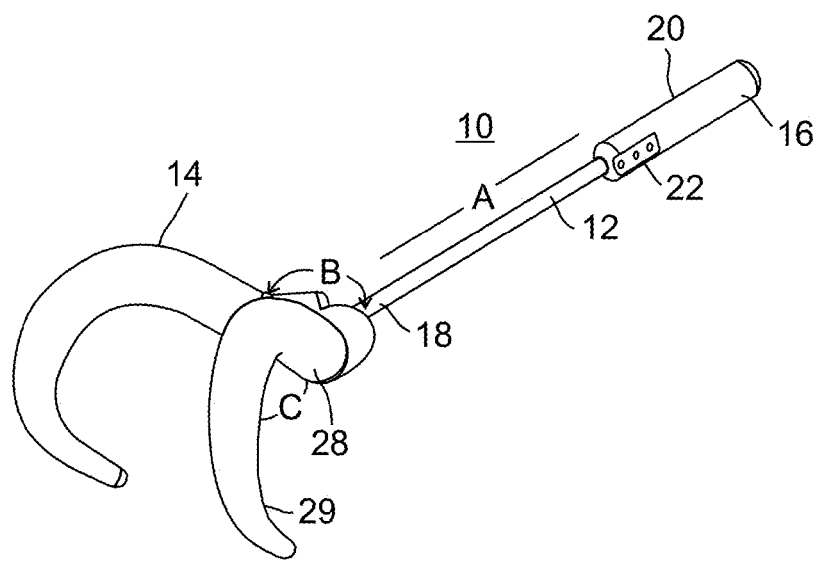
FIG. 2 illustrates a claw-like embodiment of the present device.

As is shown in FIG. 2, handle 12 can include a user engagement region 20 which includes a user interface 22 for controlling operation of device 10. Region 20 and interface 22 enable a user to maneuver device 10 and control deployment of tissue retractor head 14. For example, interface 22 can include a release valve for releasing a pressurized fluid stored in region 20 through the fluid conduits and into tissue retractor head 14. Interface 22 can also include button for activating release of fluid from an inflated tissue retractor head 14 (via actuation of valves positioned within region 20) and for actuating mechanical elements attached to, or disposed inside tissue retractor head 14 (further described hereinbelow).

Referring again to FIGS. 1a-b, as is mentioned hereinabove, device 10 also includes tissue retractor head 14. In the deployed configuration shown in FIGS. 1a-b, tissue retractor head 14 is shaped as a rake with 3 extensions 24 (three shown) protruding from a tissue head body 26. Typical dimensions for tissue retractor head 14 can be 30-100 mm in width, 30-100 mm in length with extension(s) 30-100 mm in length, and 10-60° spacing between extension(s), 3-30 mm. The volume of the tissue retractor head can be 30-200 ml or more specifically 40-80 ml.

In the configuration shown in FIGS. 1a-b, tissue retractor head is fabricated from a polymer such as thermoplastic polyurethane (TPU), reinforced nylon sheet, thermoplastic polyethylene (e.g. PET) or polypropylene and the like; tissue retractor head 14 can be fabricated by machined CRES bars.

As is shown in FIG. 1b, the angle between extensions 24 and body 26 or handle 12 is preferably slightly less than 90 degrees (e.g. 70-85 degrees). Although other angles substantially less than 90 degrees (e.g. 30-80 degrees) or more than 90 degrees (e.g. 100-130) are also envisaged herein, having an angle less than 90 degrees ensures that tissue retractor head is capable of penetrating tissue mass (e.g. coiled intestines) and hooking over tissue while providing good tissue engagement that enables efficient tissue raking or sweeping.

Tissue retractor head 14 is inflated with a fluid (e.g. Air, Nitrogen or $CO_2$ gas or water/saline) to a pressure of 0.1-3 atms, preferably 0.75 atms. Such pressure ensures that tissue retractor head 14 is rigid enough to penetrate and sweep tissue, and yet elastic and compliant enough to ensure that prolonged contact between tissue retractor head 14 and tissue does not lead to ischemia and tissue erosion.

The configuration of device 10 shown in FIGS. 1a-b provides several advantages. Tissue retractor head 14 can be packed in a small volume along handle 12 for delivery, it efficiently penetrates into spaces around tissue and it enables effective and stable sweeping of tissues and organs.

FIG. 2 illustrates a claw-like configuration of device 10. In this configuration, handle 12 is attached to tissue retractor head 14 that includes 2 hook-like extensions 24. Device 10 of this configuration is fabricated as described above for device 10 of FIGS. 1a-b. Handle 12 is as described above, while tissue retractor head 14 can also be sized as described above.

Extensions 24 of the claw-shaped tissue retractor head 14 are angled out from the longitudinal axis of handle 12 (marked with A) and include a radius of curvature of 5-10 cm. Each extension 24 includes a first portion 28 which angles up (with respect to a longitudinal axis of handle 12) by 10-60 degrees (marked with B) and is continuous with a second portion 29 which angles down by 90-180 degrees (marked with C).

The claw-shaped tissue retractor head can be fabricated from any polymer described above using similar fabrication approaches.

The configuration of device 10 shown in FIG. 2 provides several advantages. Tissue retractor head 14 and handle 12 form a very stable structure when deployed, which does not store any forces (lowest energy status—most stable). In addition, sweeping movement is aligned with the reaction axis thus reducing unwanted movement of tissue retractor head and tissue.

Tissue retractor head 14 is shown as fully inflated (deployed) in FIGS. 1-2, however, it should be noted that any tissue retractor head configuration described herein can also be partially inflated to form an intermediate shape which is, for example, more suitable for raking/sweeping than grasping etc. For example, the configuration shown in FIGS. 1a-b can be partially inflated such that extensions 24 are shorter or less rigid. Such a configuration would enable application of a containment force on tissue for longer periods of time due to the increased wall compliance of extension 24.

Selective or stepwise deployment of tissue retractor head 14 can also be realized by utilizing more than one inflatable compartment in tissue retractor head 14 or extension 24.

Figure 3:
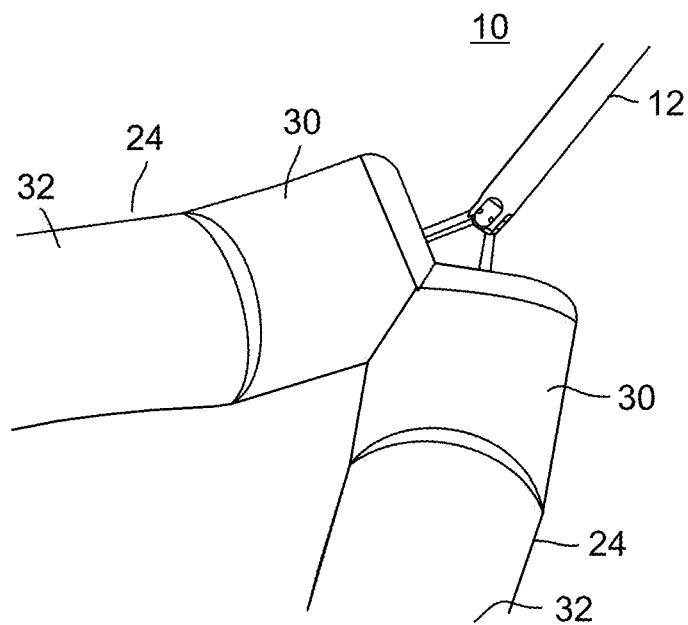
FIG. 3 is a magnified view of the base of one embodiment of the tissue retractor head of the present device showing a dual inflation chamber configuration.

For example, and as is shown in FIG. 3 extension 24 can include a first compartment 30 which can be used to control the angulation of tissue retractor head 14 and a second compartment 32 which is used to inflate extension 24.

Figure 4:
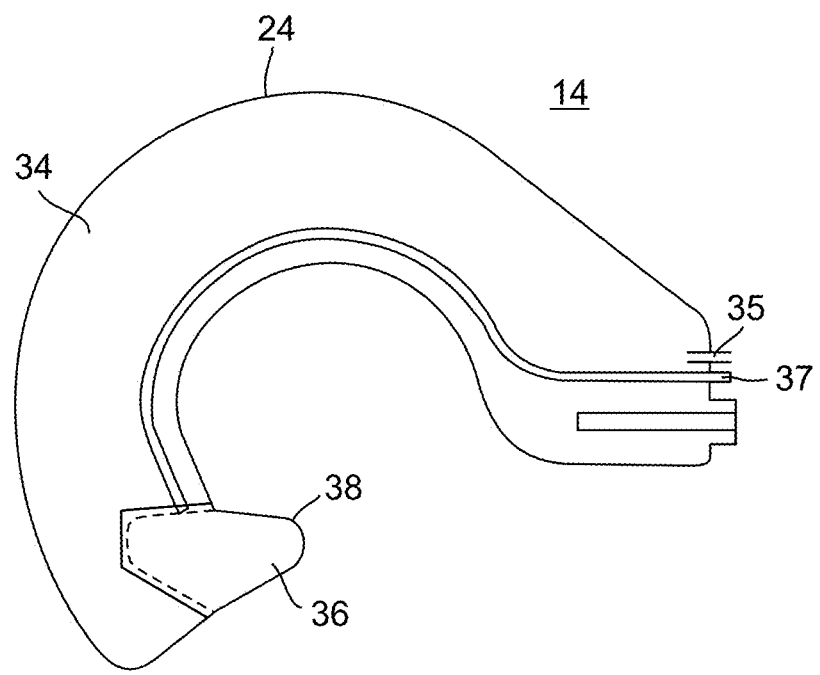
FIG. 4 is a side view of a hook shaped tissue retractor head embodiment of the present device showing another dual inflation chamber configuration.

FIG. 4 illustrates a hook-shaped extension 24 which includes a first compartment 34 for forming (via inflation through conduit 35) the general shape of the hook, and a second smaller compartment 36 which forms a wedge 38 which extends (when inflated via conduit 37) into the hook aperture. Such a configuration of extension 24 can be inflated in a stepwise manner to initially hook over a tissue (e.g. intestines) and then further inflated to form wedge 38 for grasping the tissue. Once the tissue is retracted and contained, wedge 38 can be deflated to release the pressure on the tissue.

Alternative configurations of tissue retractor head 14 or extensions 24 can include anywhere from 2 to 10 separately inflatable compartments for controlling, the shape of extensions 24, the function of extensions 24 (hooking, grasping etc) the angle of tissue retractor head and the like. Selective inflation of such compartments can be used during the procedure as needed.

Although an inflatable tissue retractor head can be rigid enough (by virtue of inflation forces) to effectively used in retracting and containing tissue while minimizing tissue trauma (see the Examples section which follows), in cases where additional forces are needed in order to efficiently retract and contain tissue retractor head 14 can include mechanical element(s) (e.g. struts, mesh) for added rigidity when in a deployed position.

Figure 5A:
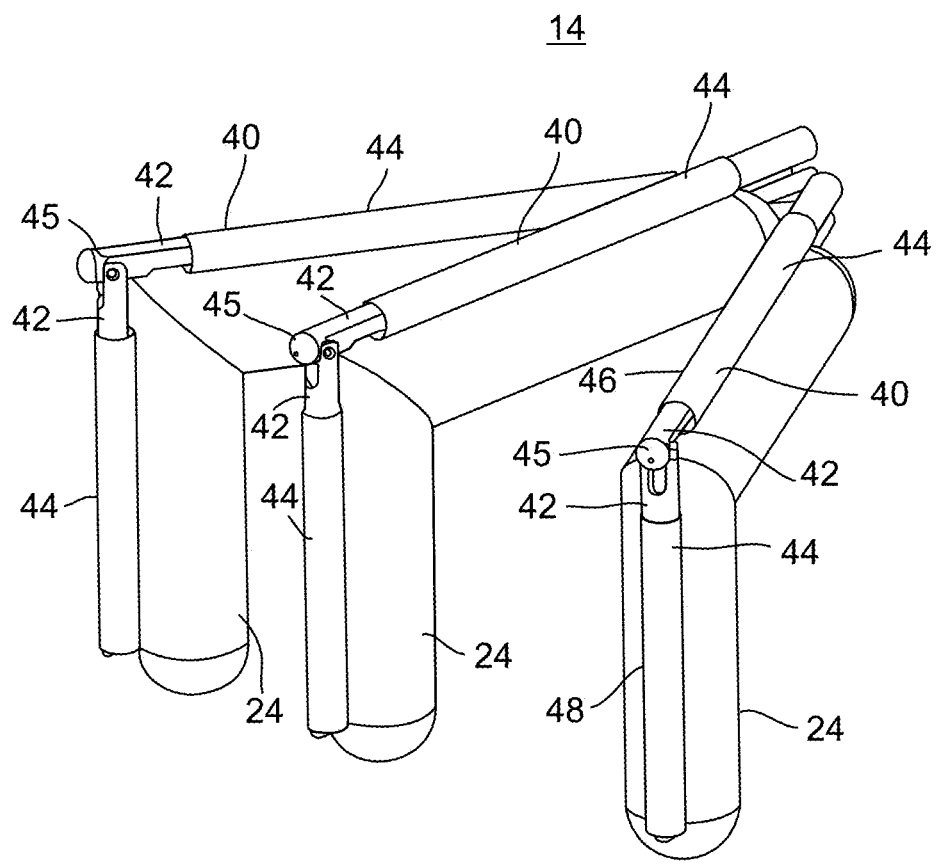
FIGS. 5A-B illustrate a rake-like tissue retractor head with mechanical support in isometric (FIG. 5A) and side (FIG. 5B) views.
Figure 5B:
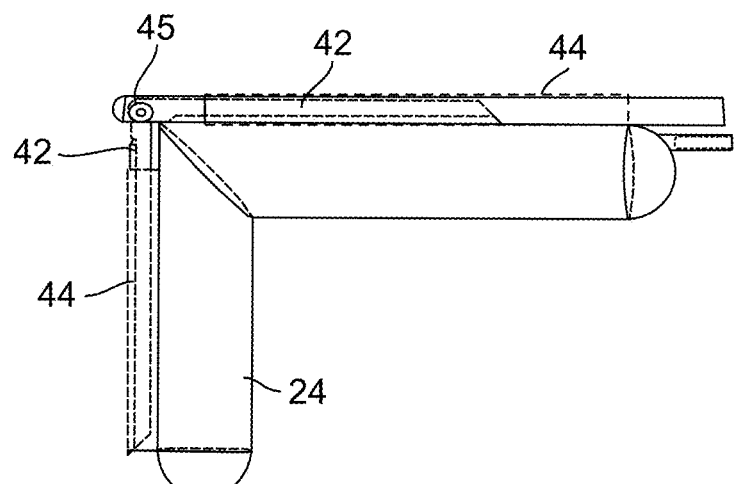
Figure 6:
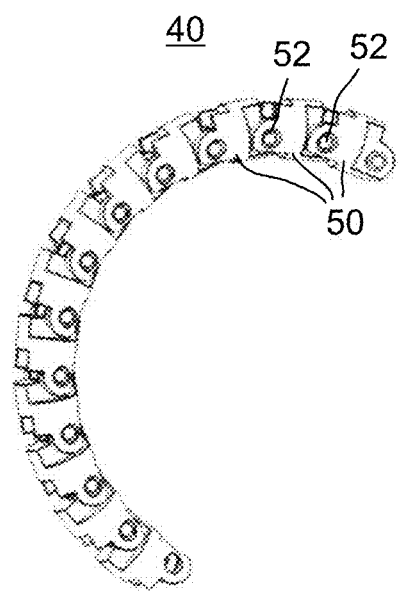
FIG. 6 illustrates a hook-shaped mechanical support utilizable in one embodiment of the present device.

FIGS. 5-7 illustrate several embodiments of device 10 which include mechanical elements for increasing rigidity (and thus tissue loading capabilities) of tissue retractor head 14 and/or extensions 24.

FIGS. 5a-b illustrate a device 10 that includes mechanical struts 40. Struts 40 serve an exoskeleton-like function and add rigidity and load capabilities to extensions 24. In that respect each strut 40 include one or more fairly rigid (yet foldable) polymer or alloy (e.g. stainless steel, titanium etc) sections 42 surrounded by a soft sheath 44 composed of a polymer such as TPU or silicone or nylon sheet. Each strut 40 is attached to an extension 24 via an adhesive or a mechanical coupler or welding (US, heat or RF) or sewing. Alternatively, sheath 44 can be co-molded with extension 24 and strut 40 inserted into sheath 44.

In the configuration shown in FIGS. 5a-b, each strut 40 includes two sections 42, with section 46 attached to section 48 via a hinged region 45. In a delivery state (prior to deployment) sections 46 and 48 are preferably co-linear. Such a strut 40 configuration can be deployed and locked in a desired angulation (90 degrees in FIG. 5b) to determine the shape and angulation of extensions attached thereto. Deployment and setting of struts 40 can be actuated by inflation of extensions 24, i.e. inflation of extensions 24 deploys struts 40 and sets their position; following which struts 40 can be locked in position. Alternatively, struts 40 can be deployed (extended and angled via, for example cable actuated from handle 12 or rigid plunger) and locked, following which extensions 24 are inflated into the shape dictated by struts 40. In any case, once deployed, struts 40 add rigidity to extension 24 and enable use thereof in cases where added tissue retractor head loading is required.

FIG. 6 illustrates another configuration of a mechanical strut 40 which can be used to add rigidity to a tissue retractor head 14 having hook-shaped extensions 24 (e.g. such as those shown in FIG. 2). Such a strut 40 configuration can be attached to an external surface of an extension 24 or preferably positioned within extension 24 and function as a skeleton (i.e. surrounded by the balloon forming extension 24). Strut 40 of FIG. 6 includes a plurality of links 50 which are interconnected via hinges 52. Links 50 can form a desired shape (e.g. hook) via cable (pull) or tendon (push) actuated by handle 12 or by inflation of extension 24. In any case, once in a desired position, links 50 can be locked from handle 12 via a cable.

FIGS. 7a-b illustrate yet another configuration of device 10 which utilizes a mechanical element for adding rigidity to tissue retractor head 14. In this case, a strap wire or string 54 (or any other non-rigid, semi-rigid or rigid element) can interconnect a region of tissue retractor head 14 to handle 12 to provide rigidity (the wire/strap/string provides a counter force in one direction while the inflated balloon retractor head presses against the handle in the other direction) when device 10 is used for sweeping or raking tissue.

Tissue retractor head 14 of device of FIGS. 7a-b can be configured from two glued or welded flat halves which provide a flat 2D configuration (planner) when deflated and thus facilitate packing of tissue retractor head 14 for delivery and retraction. Once deployed and inflated, tissue retractor head 14 assumes a 3D configuration with a volume of 30-200 ml and angulation of 90 degrees or less with respect to handle 12 as determined by length of wire/string 54. The length of wire/string 54 can be preset or modified by the user from handle 12 prior to or following delivery of device 10.

Wire 54 can also extends to the proximal end and be pulled by the user to achieve a specific desired position of the rake (changing the angle during fixation). In this case, release is effected externally. Following use of device 10, release of wire 54 from tissue retractor head 14 (by cutting along length or releasing from handle) releases tissue retractor head and linearized device 10 (i.e. tissue retractor head 14 co-linear with handle 12) thus facilitating removal of device 10 following deflation of tissue retractor head 14 (which can be effected via unplugging of the conduit from source or by puncturing the balloon).

It will be appreciated that although tissue retractor head 14 shown in FIG. 7a-b includes two welded/glued halves with weld/glue seams pointed outward, a configuration in which the glue/weld (same) seams point into a lumen of tissue retractor head 14 is also envisaged. The formed configuration is advantageous in that it increases the rigidity of tissue retractor head 14, while the latter configuration is advantageous since it can potentially reduce tissue trauma caused by the relatively hard seams.

While further reducing the present invention to practice and testing various configurations of rake-shaped prototypes under ex-vivo and in-vivo conditions (see Examples 5-7), the present inventors further refined the configuration of FIGS. 7a-b.

Figure 7C:
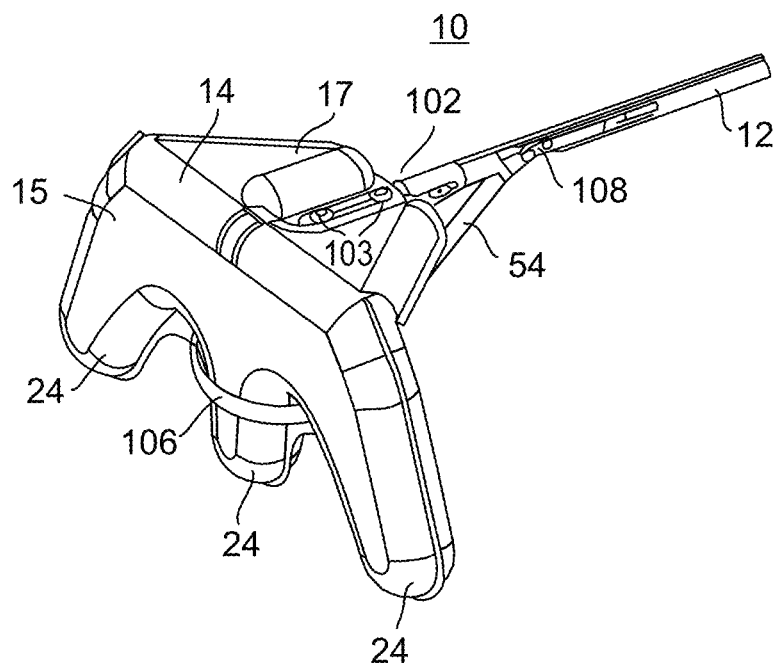

FIGS. 7c-i illustrate one presently preferred configuration of the device generally described in FIGS. 7a-b.

Figure 7D:
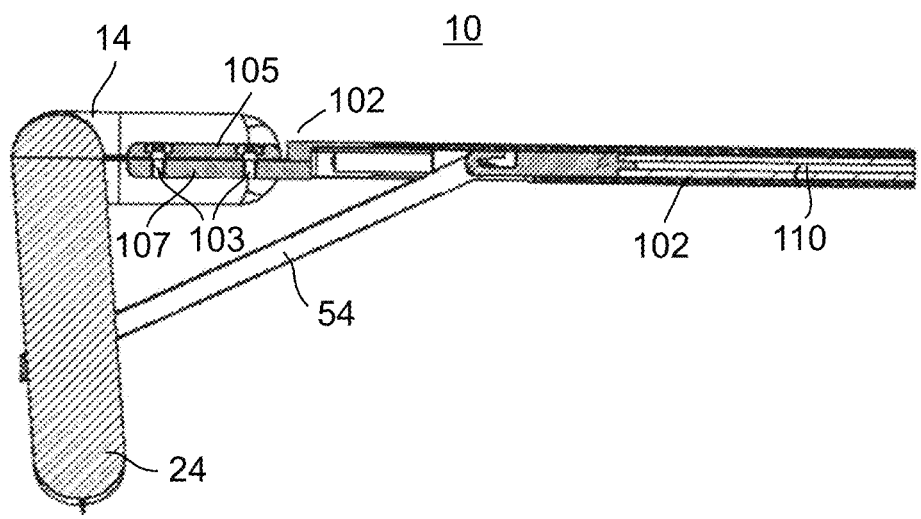

FIGS. 7c-d illustrate in greater detail retractor head 14 and a portion of handle 12. As is mentioned hereinabove, retractor head 14 is fabricated having a flat 2D configuration (planner) when deflated to facilitate packing of tissue retractor head 14 for delivery and retraction. When inflated with a fluid (e.g. air), retractor head 14 assumes a 3D configuration which includes 3 spaced apart finger-like extensions 24 which form a part of portion 15 of retractor head 14. Retractor head 14 also includes portion 17 which is preferably contiguous with portion 15 and is used for attaching retractor head 14 to handle 12. In order to enable retractor head 14 to form the angulated structure shown in FIGS. 7c-d when inflated (further discussed hereinbelow), portion 17 functions as a binge region' around which retractor head 14 angulates when inflated against the pulling force of strap 54.

This embodiment of retractor head 14 has the following characteristics:
(i) a volume of 30-200 ml;
(ii) an overall length (covering portions 15 and 17 prior to angulation) of 100 mm;
(iii) an extension length (the length of the fingers) of 50 mm;
(iv) external fingers angle outward 75 per side (150 between two side fingers) degrees (from the vertical);
(v) a thickness of fingers of 200 mm in their inflated form;
(vi) a distance between outer fingers of 80 to 200 mm; and
(vii) a retraction surface area of 8,000 mm².

Device 10 is fabricated by cutting and welding (RF welding) 2 sheets of substantially non-compliant polyurethane sheet. The inflation conduit (which runs through handle 12) is connected to retractor head 14 which is then attached to a distal portion 102 of handle 12 via screws 103. As is shown in greater detail in FIG. 7h, screws 103 sandwich plates 105 and 107 around a flat (non-inflatable) portion of retractor head 14. Elements 105 and 107 are fabricated from high strength stainless steel (e.g. SS17-4 or 17-7 or SS316) and element 107 is laser welded to handle 12.

Handle 12 is fabricated as a tube from stainless steel (e.g. 316LVT), with a length of 350-500 mm, an external diameter of 6 mm and an internal diameter of 4 mm.

Inflation of retractor head 14 is effected using a 60 ml syringe connected to a 3-way valve (e.g. a port with selector; port 158 and toggle 156 respectively-described hereinbelow). The toggle is actuated to a position which connects the inlet to a side opening and the syringe is expanded (by pulling the plunger back). The toggle is then turned to connect the inlet and the outlet (outlet—to retractor head 14) and the fluid-filled syringe is actuated to pump retractor head 14 and the toggle is moved to block fluid from escaping from retractor head 14 and connect the syringe to the side opening. The syringe can then be re-expanded and the process repeated if higher pressure is needed. Once retractor head 14 is fully inflated the outlet can be blocked by a stopper and the syringe removed. Deflation can be effected by releasing the valve or by reversing the steps of inflation. Since the inflation conduit is relatively narrow, inflation is preferably effected using a gas (e.g. air, nitrogen or $CO_2$). This enables rapid inflation (5-15 seconds) and deflation (5-15 seconds). A suction source (suction pump, syringe) can be used to further facilitate deflation as described above.

A strap 54 fabricated from polyurethane and having a length of 60-160 mm, a width of 2-6 mm and a thickness of 0.1-0.4 mm (double layers of a thermoplastic polyurethane material such as PET) is inserted through slots in retractor head 14 and wrapped around middle extension 24 (at 106) and the ends of strap 54 are attached to a hook mechanism 108 provided within handle 12 (Shown in FIGS. 7c-d and 7h-i). Strap 54 can be fabricated as a standalone element or as part of retractor head 14. Strap 54 can be also welded at a single point to retractor head 14, this ensures that if strap 54 tears it is not left behind within the abdominal cavity and always pulled out with the device.

Hook mechanism 108 is attached to a wire/rod 110 (shown in detail in FIG. 7i) which is actuate-able (pull/push) from the user interface of handle 12 via a slider and locking button as is further described hereinbelow.

Figure 7E:
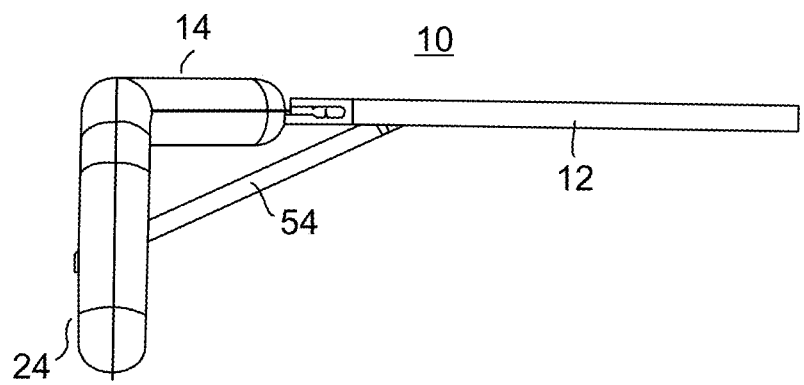
Figure 7F:
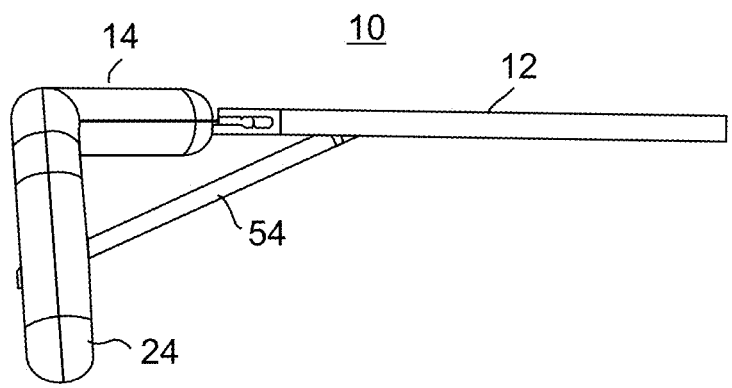
Figure 7G:
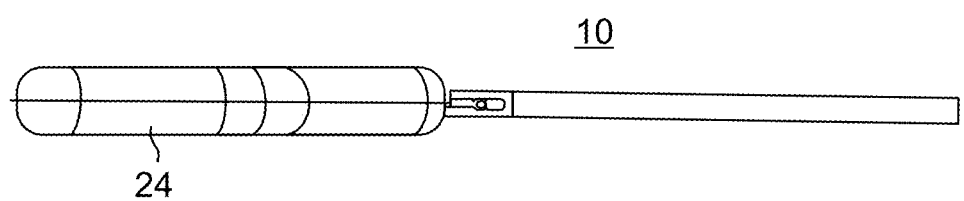

As is shown in FIG. 7e, when retractor head 14 is inflated (following positioning within body cavity), strap 54 maintains retractor head 14 in an angulated position (roughly 90 degrees to handle). Wire/rod 110 can be pulled in to pull strap 54 and extensions 24 inward (as is shown in FIG. 7f) or released/pushed to release strap 54 and thus release extensions 24 outward (not shown). If strap 54 is completely released (by releasing it from hook mechanism 108 or by cutting strap 54), retractor head 14 assumes a completely linear configuration (as is shown in FIG. 7g). Such a linear configuration is useful for facilitating removal of device 10 from the body cavity (following deflation of retractor head 14).

When pulling or retracting tissue, the preferred angle of extensions 24 with respect to handle 12 is as shown in FIG. 7f, i.e. slightly less than 90 degrees (about 85 degrees).

However, other angles, for example about 45 degrees or 120 degrees, can be set by actuating wire/rod 110 in order to grasp or release tissue (respectively).

In any case wire/rod 110 enables retractor head 14 to form a rake-like structure when inflated and to adjust the angulation of extensions 54 with respect to handle 12 in different use scenarios.

Figure 7H:
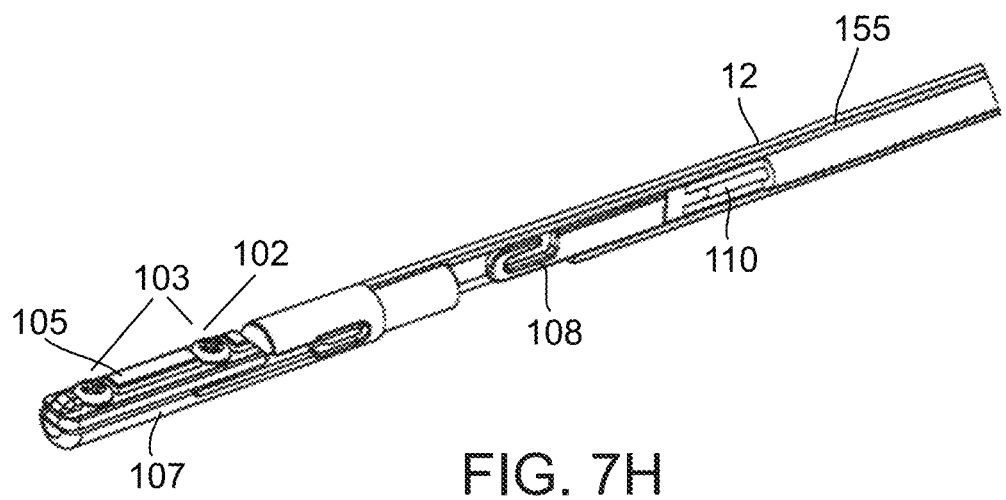
Figure 7I:
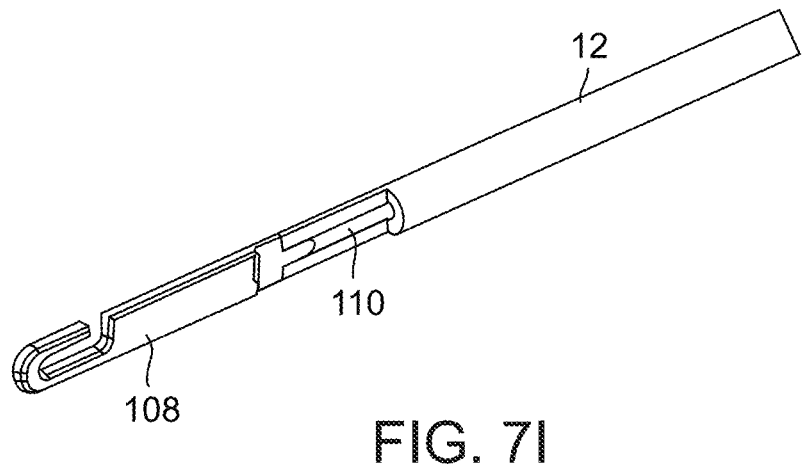
Figure 7J:
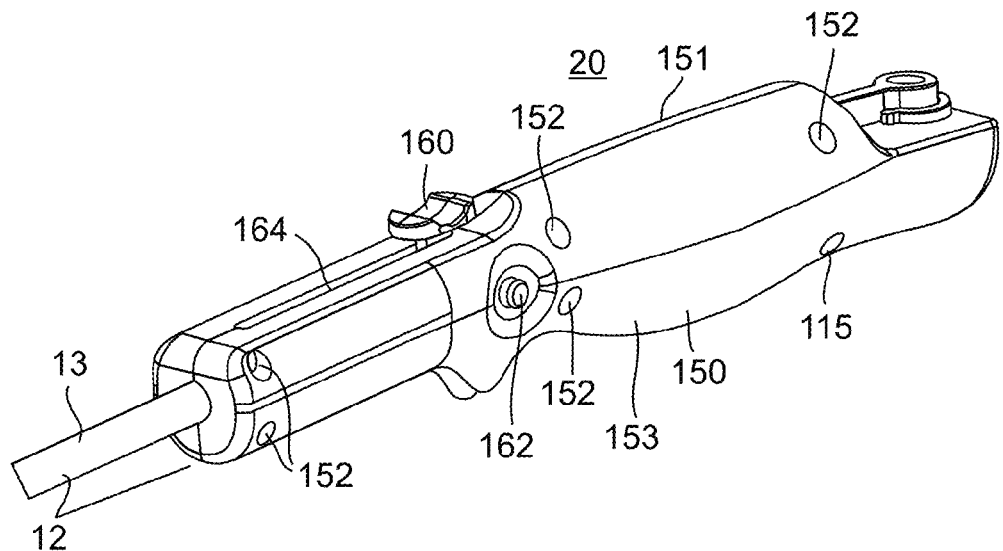
FIGS. 7J-L illustrate the user engaged portion of the handle of the device shown in FIGS. 7C-I.
Figure 7K:
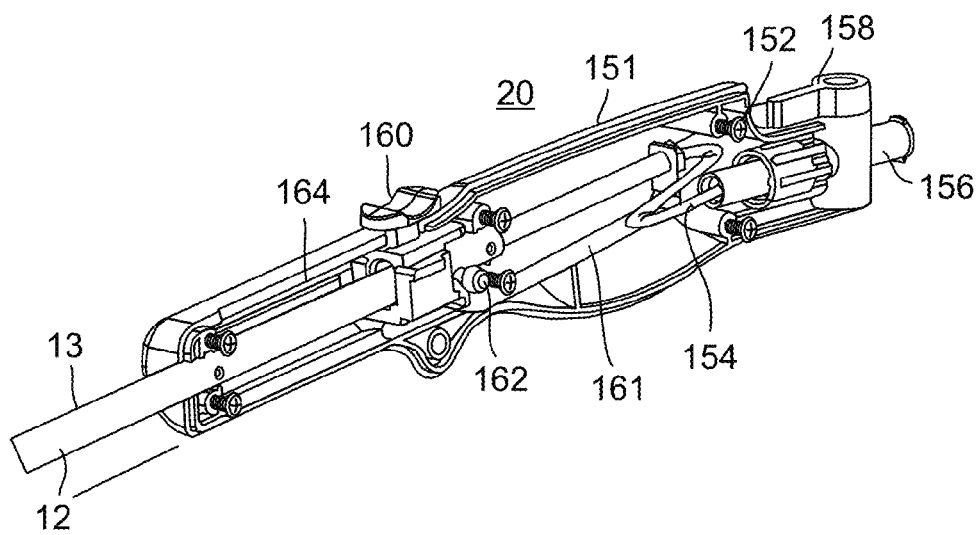
Figure 7L:
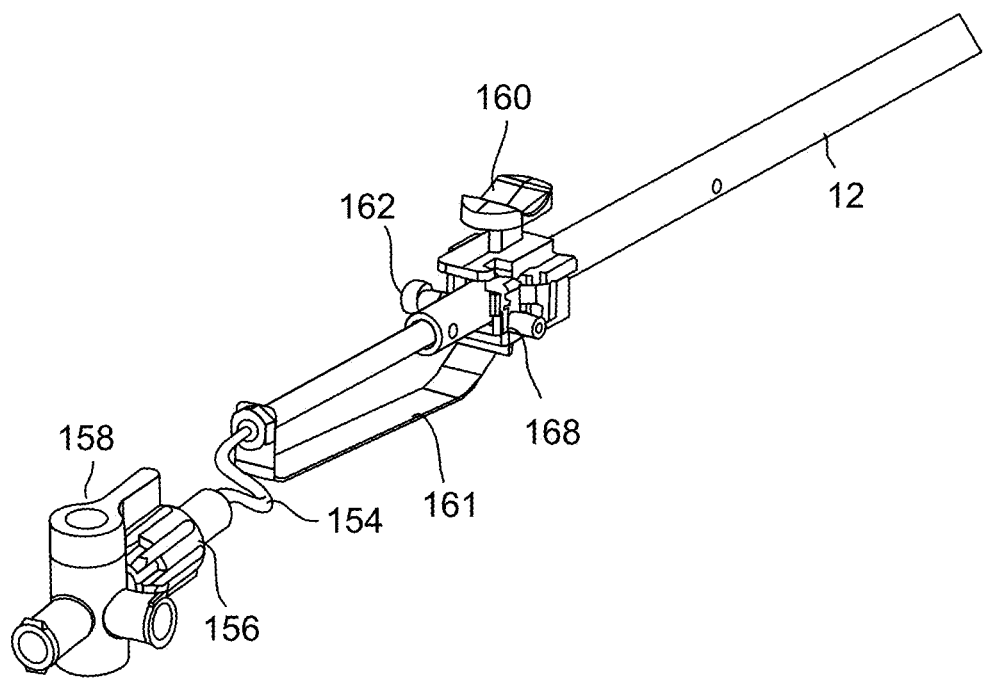

FIGS. 7j-l illustrate a user engagement region 20 of handle 12. Region 20 includes a polymeric or alloy housing 150 which can be constructed from two shell halves (151 and 153) joined via screws 152. As is shown in FIG. 7k, halves 151 and 153 house mechanisms utilized for inflation and angulation of retractor head 14, while the controls for such mechanisms are disposed outside of housing 150 and are operatively connected thereto.

Housing 150 covers an inflation conduit 154 which is connected to an inflation port 156 positioned through a proximal end of housing 150 and runs through shaft 13 to connect to retractor head 14. A manually operated valve toggle 158 (which is connected to port 156 and is positioned outside of housing 150) controls flow in and out of port 156 and thus allows the user to control inflation and deflation of retractor head 14. Port 156 can be connected to a syringe or a pump and includes the necessary hardware for such connections (e.g. Luer lock in case of a syringe). The arrangement of air conduit 154, port 156 and toggle 158 is shown in greater detail in FIG. 7*l* which illustrates these isolated components from the proximal end of device 10.

Housing 150 further covers a mechanism for actuating strap 54 (not shown in these Figures). Such a mechanism includes a rod-actuated hook (positioned within shaft 13) which is attached to strap 54 (not shown in these figures). Actuation of the rod and attached hook is effected using slider 160 and locking button 162. Slider 160 can be manually translated back and forth within slot 164 to either tension strap 54 (to angle extensions 24 inward—in the direction of user engagement region 20) or to release tension on strap 54 to angle extensions 24 outward). When translated forward (in the direction of the distal end of device 10), slider 160 loads a leaf spring 161 (FIG. 7*l*). Button 162 can lock slider 160 at any position along slot 164 thus enabling locking of extensions at any preset angle (between 45-180 degrees). When activated (for locking), button 162 locks and loads a spring 168 (FIG. 7*l*) which enables release of button 162 via a second activation. When locked at an angle of extensions 24 of less than 180 degrees, release of button 162 automatically linearizes (180 degrees) extension 24 due to the return of leaf spring 161.

FIGS. 7*m-p* illustrate strap 54 lock and release mechanism showing the functionality of slider 160 and locking button 162. As is described above, slider 160 sets a tension on strap 54 and thus the angle of extensions 24 with respect to shaft 12, while locking button 162 locks slider 160 and thus locks extension 24 at the desired angle.

Figure 7M:
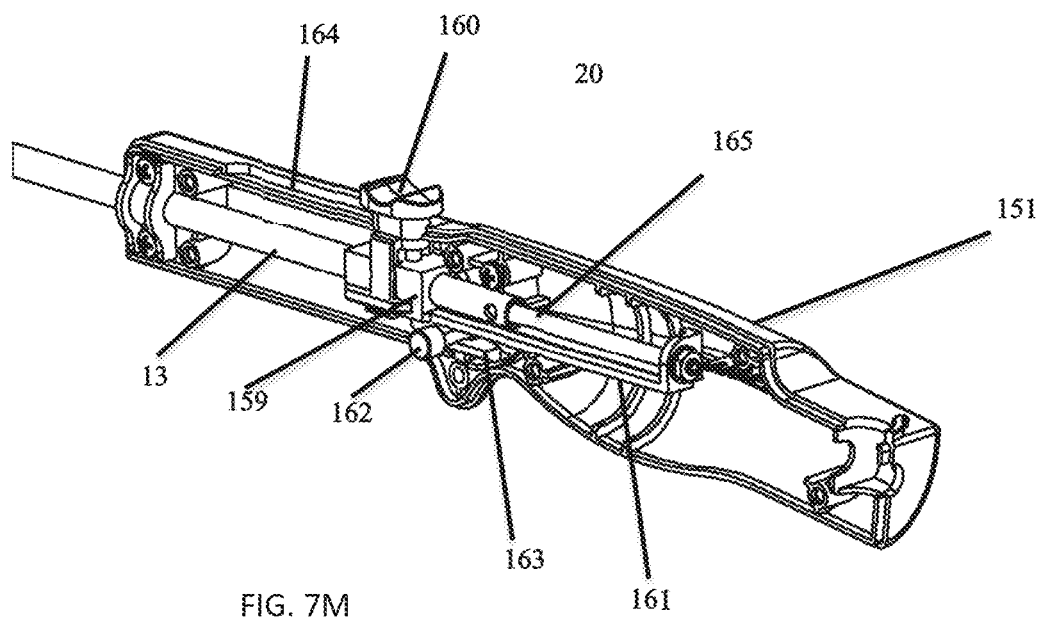
FIGS. 7M-P illustrate in greater detail the slider and locking button for actuating and locking the retractor head angle with respect to the elongated body of the present device.
Figure 7N:
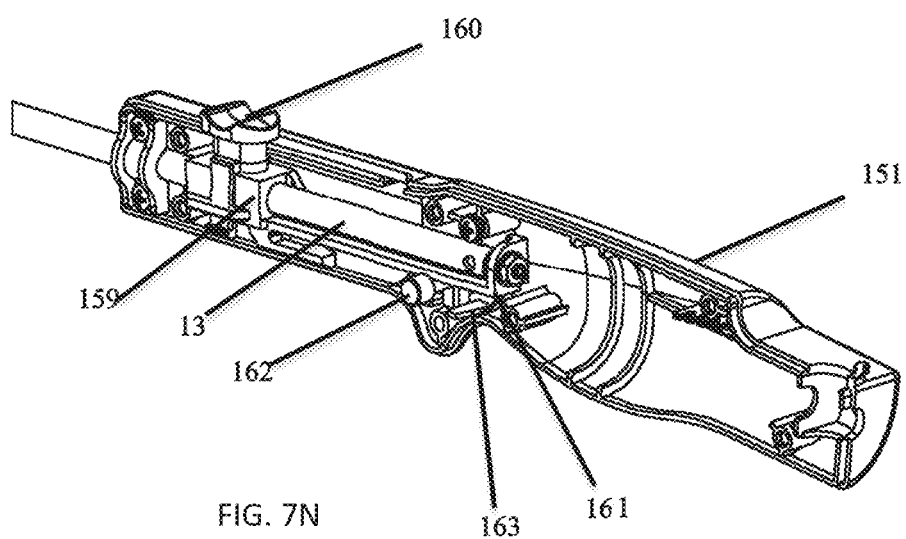

In FIG. 7*m*, slider 160 is fully retracted back within slot 164 and as such strap 54 (not shown in this Figure) is fully tensioned and extensions 24 are angled at about 90 degrees with respect to shaft 12. At such a position, internal sliding tube 165 is fully retracted out of shaft 13 and covers air conduit 154 (FIG. 7*l*) which is connected to the base of 17 (FIG. 7*c*) at the distal end thereof, and to port 156 (FIG. 7*k*) at a proximal end thereof.

When locking knob 162 is released, slider 160 can be pushed in and moved within slot 164 with attached housing 159 moving along shaft 13. When slider 160 is advanced forward (to release tension from strap 54), internal sliding tube 165 which is attached to housing 159 via bracket 161 advances into shaft 13 (FIG. 7*n*) to reveal air conduit 154 (FIG. 7*l*). In order to facilitate assembly, extra length of air conduit 154 is needed. Once installed air conduit 154 needs to be maintained under tension in order to prevent it from buckling when internal sliding tube 165 slides over it. Air conduit 154 is tensioned, and the extra length is secured to 151 such that it 'floats' relative to internal sliding tube 165 and bracket 161 (FIG. 7L).

Figure 7O:
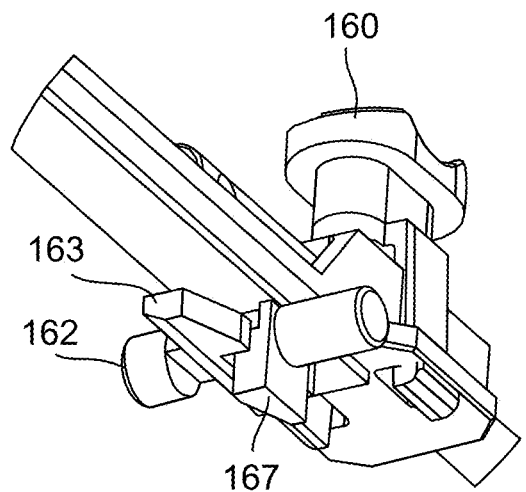
Figure 7P:
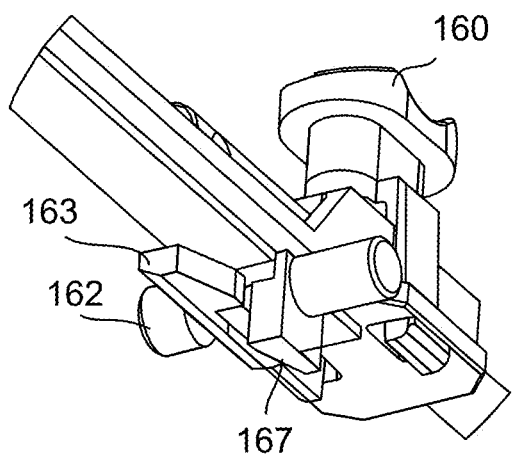

FIGS. 7*o-p* illustrate locking knob 162 and latch 163 in greater detail. In the locked position, latch 163 engages element 167 which forms a part of housing 159 attached to slider 160. When locking knob 162 is depressed, latch 163 releases element 167 and enables housing 159 to move along shaft 13 and attached slider 160 to move within slot 164; following release, latch 163 (which is spring loaded or made from a sprung material) return to its locking position. When slider 160 is pulled back, element 167 automatically engages latch 163 and locks slider 160 in position.

In order to enable a user to set the locking position, locking knob 162 and latch 163 can form a part of a movable assembly which can be positioned anywhere along shaft 13.

As is mentioned hereinabove, device 10 of the present invention can be used in retraction of organs in abdominal procedures. During such procedures fluids can accumulate in the abdominal cavity to cover and block the surgeon's view of the surgical field. In order to traverse this problem, active suction is used to aspirate fluids out of the abdominal cavity during the procedure.

Since it is common to insufflate the abdominal cavity with a gas (e.g. CO2) in order to provide access to the organs, a pressure gradient of 100-200 cm $H_2O$ is maintained across the abdominal wall during the procedure.

While experimenting with a prototype of the device of FIGS. 7*a-g*, the present inventors observed that the device tended to passively suction-out abdominal fluids which were pushed out through the internal and external tubing of the device handle.

In order to address this problem, an opening (ventilation hole) 155, 0.5-1 mm in diameter, can be provided along a length of shaft 13 (see FIG. 7H). Such an opening equalizes the pressure within shaft 13 with the surrounding environment and prevents passive suction.

The pressure gradient maintained across the abdominal wall during minimally invasive surgery can be used for passive diffusion of fluids out of the abdominal cavity.

Such passive diffusion can be effected by providing device 10 of the present invention with a fluid conduit that opens on the distal end of device 10 near retraction head 14 and at the proximal end near user engagement region 20 of handle 12 (in such a configuration shaft 13 does not include ventilation holes 155). The opening of the fluid lumen near the proximal end can be connected to a collapsed collection bag (via, for example, tubing). When device 10 is positioned within fluids present in the abdominal cavity, the pressure gradient would drive the fluid up through the fluid conduit and into the bag which can be replaced when full. In order to prevent filling of the bag with the insufflation gas, the fluid conduit can be provided with a valve which can be opened or closed from user engagement region 20 of handle 12.

The passive diffusion approach described above can also be realized via a standalone configuration.

Figure 7Q:
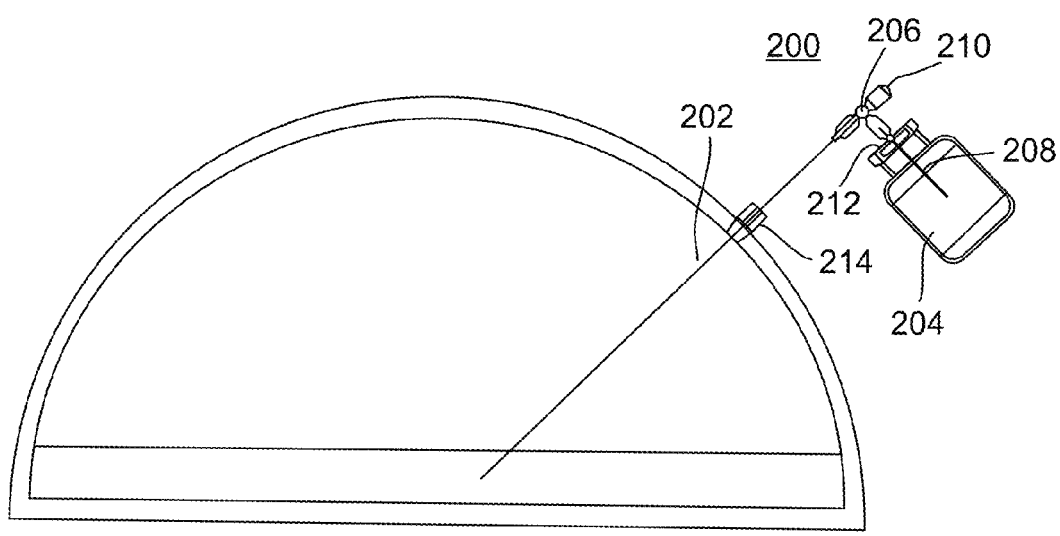
FIG. 7Q illustrates a passive diffusion system that can be used to remove fluids from a surgical space.

A standalone passive diffusion system which is referred to herein as system 200 is illustrated in FIG. 7*q*.

System 200 includes a cannula 202 which is typically 380 mm in length (different lengths can be also used depending on use), 3 mm in outer diameter with a fluid conduit-forming lumen 2 mm in diameter. Cannula 202 can be fabricated from an alloy or polymer. Cannula 202 is attachable to a reservoir 204 through a valve mechanism 206 which can be toggled to direct fluids from cannula to reservoir 204 through conduit 208, to direct fluids to a second opening 210 or to block diffusion of fluids out of the body cavity.

Opening 210 can include a Luer-type lock to enable connection of a syringe for injection of fluids (such as irrigation fluids) into the body cavity.

Reservoir 204 can be rigid container in which case it also includes a venting valve 212 to prevent pressure buildup within reservoir 204. Alternatively, reservoir 204 can be a collection bag (similar to, for example, a urine bag) which is collapsed under partial vacuum and expands during filling.

System 200 further includes a trocar 214 for enabling access therethrough into the body cavity; trocar 214 can be 3-5 mm trocar.

The system can be used in any laparoscopic procedure that requires fluid aspiration. For example in laparoscopic colectomy a suction device is frequently used in order to maintain the target organ clear of fluid (blood and saline) that can block the surgical field. In such cases, system 200 can be used to reduce the need for repeated deployment of a suction device. In addition, presently used active suction devices can be limited by the presence of gas mixed in with fluids which can change the suction rate and cause clogging.

FIGS. 8a-g illustrate the various components of one embodiment of the device shown in FIGS. 5a-b in greater detail.

FIG. 8a illustrates device 10 in a folded pre-deployed delivery configuration (through a trocar port), while FIGS. 8b-d provide magnified views of the retractor head 14 of the device, showing the tissue retractor head (without included balloon). FIG. 8f illustrates tissue retractor head 14 of device 10 showing expanded balloon (forming extension 24) prior to folding (fold at hinge 45) which creates the claw shaped extension 24 shown in FIGS. 5a-b.

The specific embodiment of device 10 shown in FIGS. 8a-f include two buttons 60 and 62 for setting (via rod 61, FIG. 8c) and locking an angle between sections 46 and 48 (which pivot via hinge 45). In the folded configuration shown in FIGS. 8a-b, the balloon forming extension 24 (not shown) is folded over sections 46 and 48 (folded against each other). Once the balloon extension 24 is deployed (inflated), section 48 forms an angle with respect to section 46 (FIGS. 8c and 8e), which can be set and locked via buttons 60 and 62 (respectively). As is shown in FIGS. 8f-g, sections 46 and 48 are covered by sleeves 47 and 49 (respectively). Sleeves 47 and 49 cover and pack balloon 24 (FIG. 8g) when sections 46 and 48 are folded in the delivery configuration of device 10.

The device is inserted into the body in the configuration shown in FIG. 8a, deployment of the device to the configuration shown in FIGS. 5A-B is effected within the body cavity. Once the procedure is over, the rod locking sections 46 and 48 in the preset angle is released and the balloon straightens the device to the configuration shown in FIG. 8f. The balloon extension(s) 24 can then be deflated (via valve release at handle 12) and device 10 removed from the body cavity through the trocar port.

As is mentioned hereinabove, device 10 of the present invention can be used in a variety of minimally invasive surgeries. FIGS. 9a-g illustrate use of device 10 (of FIGS. 7a-b) in retracting and containing intestinal tissue in order to create a surgical workspace in an abdominal procedure. For the sake of simplicity only the delivery, deployment and use of device 10 is shown in FIGS. 9a-g. It will be understood however, that additional devices delivered through dedicated ports are also used in a procedure along with device 10.

Figure 8H:
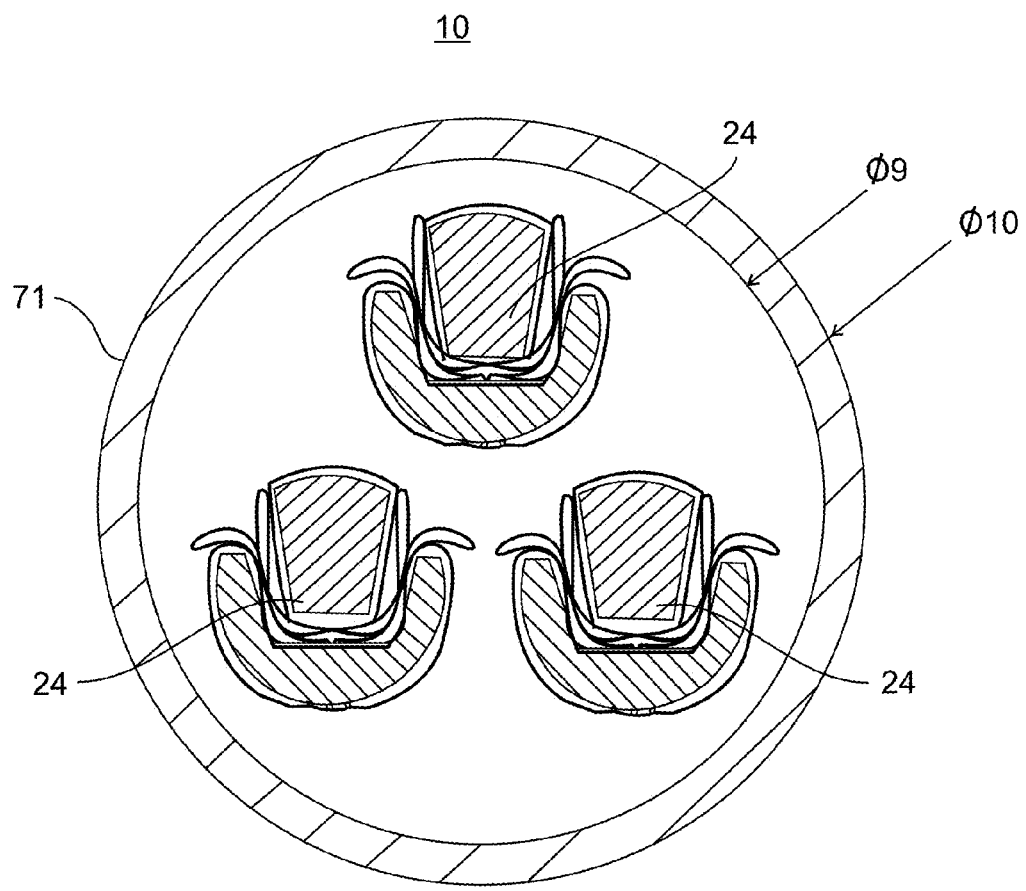
Figure 9A:
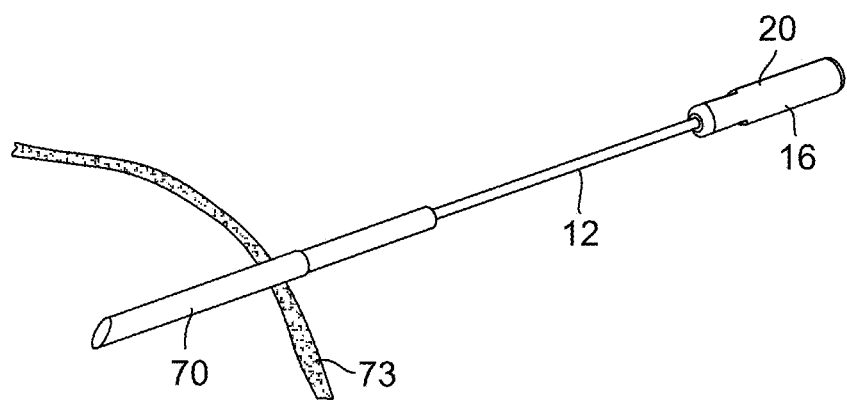
FIGS. 9A-G illustrate use of one embodiment (shown in FIGS. 7A-B) of the present device in a simulated laparoscopic procedure.
Figure 9B:
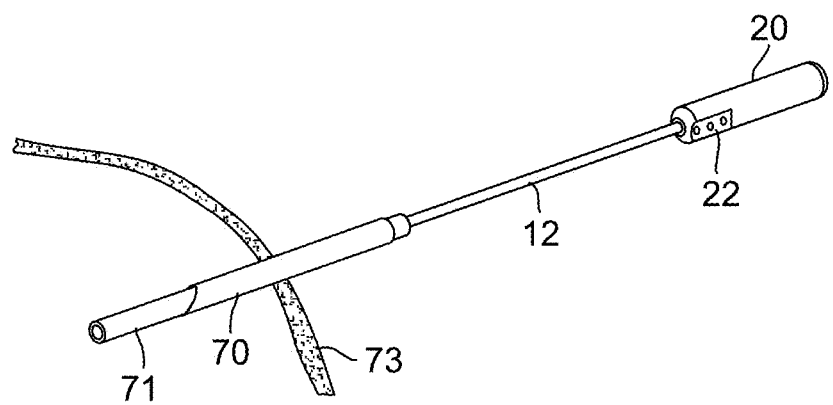
Figure 9C:
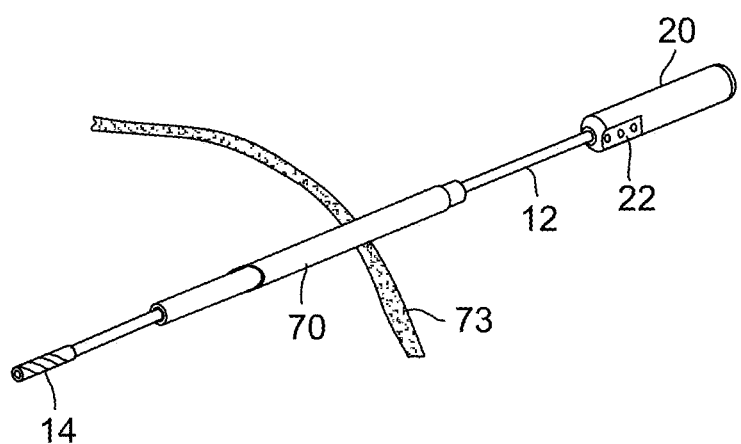
Figure 9D:
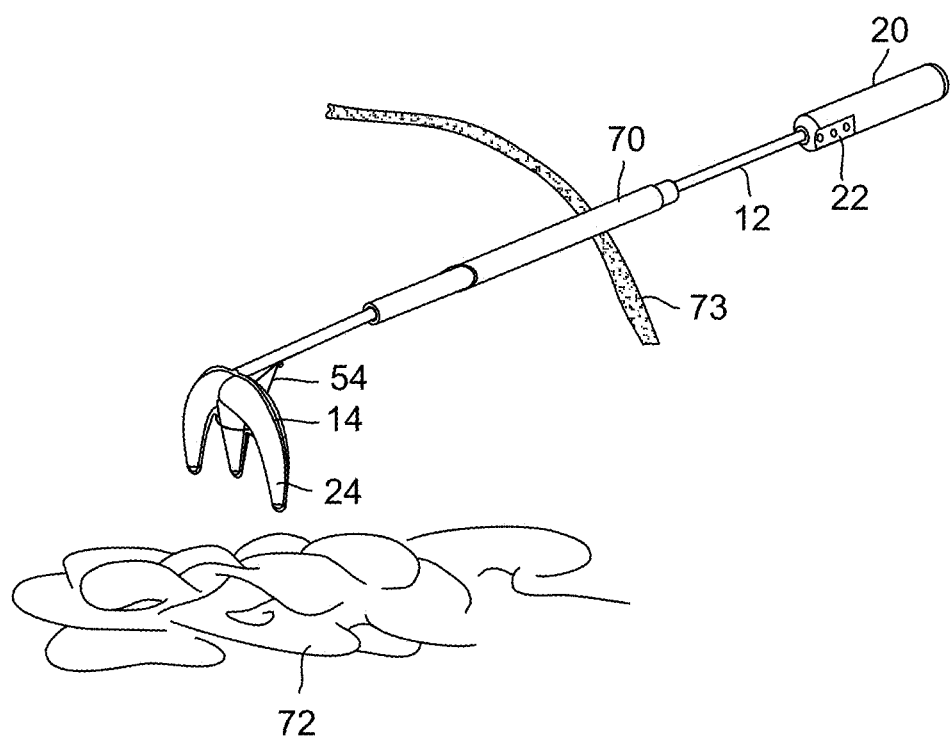
Figure 9E:
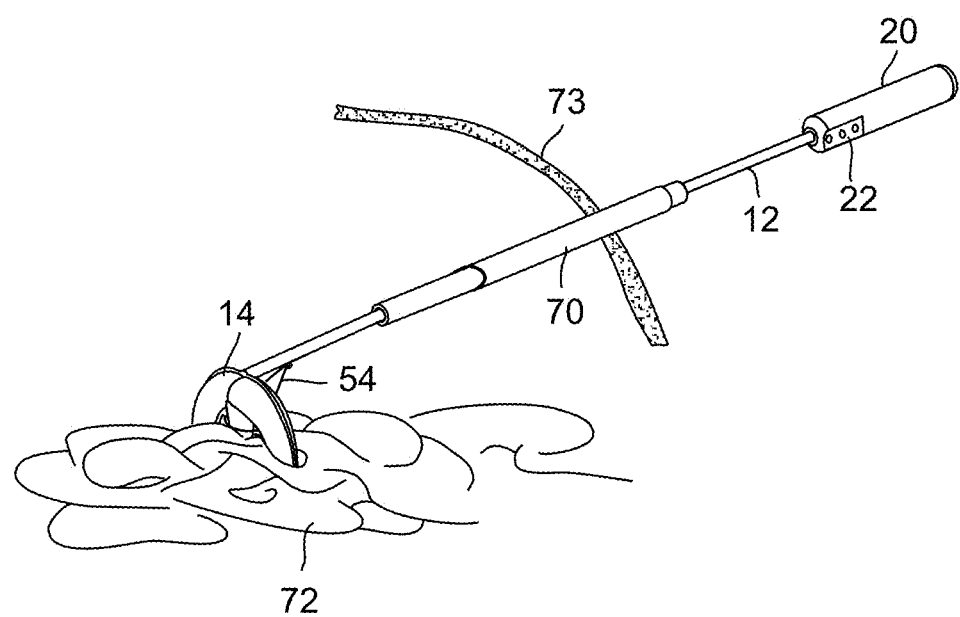
Figure 9F:
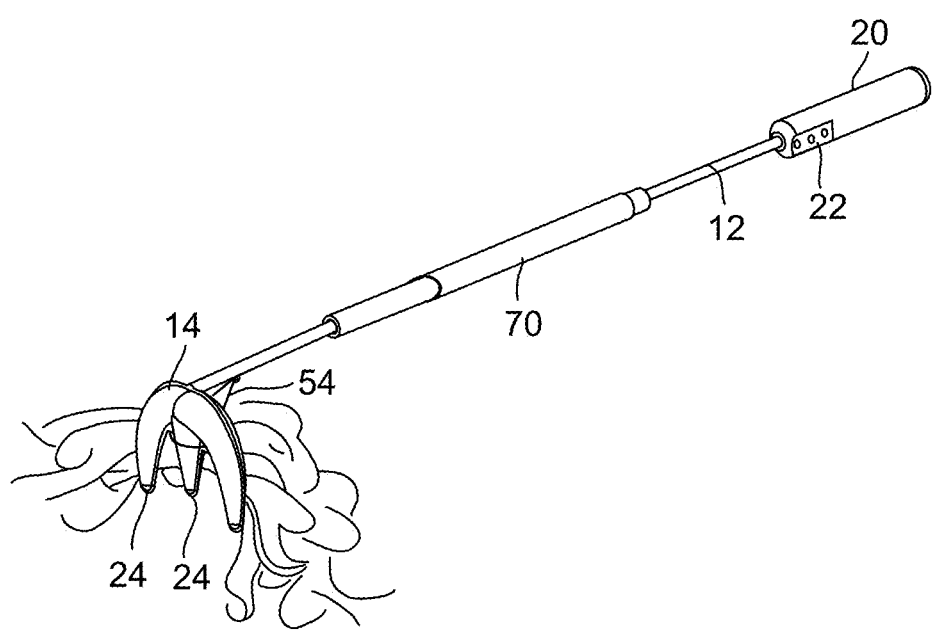
Figure 9G:
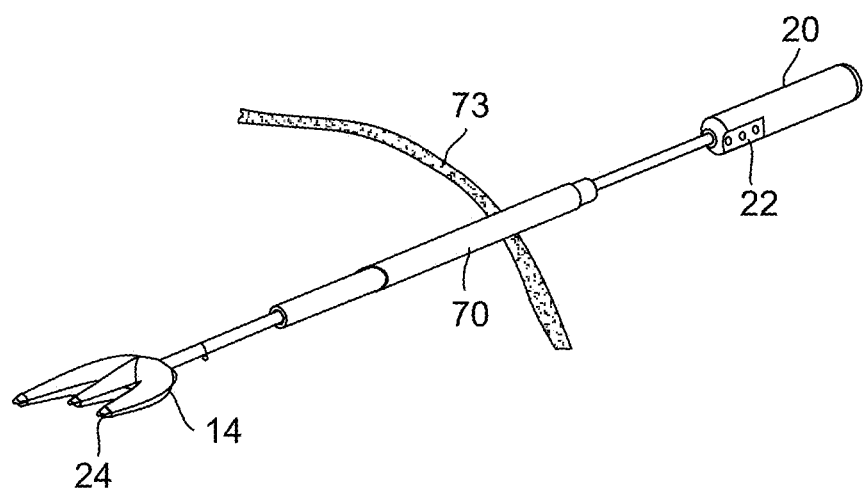

FIG. 9a illustrates device 10 in a pre-deployed (folded) configuration positioned within a trocar port 70 which is in turn positioned through an incision in the abdominal wall. Delivery of device 10 through trocar 70 and into the abdominal cavity (through abdominal wall 73) is illustrated in FIGS. 9b-c. During delivery, deflated extensions 24 are packed within a sleeve 71 having an external diameter of about 10 mm and an internal diameter of about 9 mm (as is shown in FIG. 8h). FIG. 9d illustrates device 10 in deployed configuration showing a rake-like tissue retractor head 14. Tissue retractor head 14 is positioned over the intestines (under the guidance of video imaging provided via an endoscopic camera positioned through a dedicated port—not shown) and tissue retractor head 14 is pushed into spaces around intestines 72 thereby forcing extension 24 in spaces around intestinal tissue folds (FIG. 9e). Intestines 72 are then raked aside by pulling device 10 through handle 12 positioned outside the body (FIG. 9f). Once the procedure is complete, wire 54 holding tissue retractor head at an angle to handle 12 is released (cut or released from handle 12) and tissue retractor head 14 assumes a co-linear configuration with handle 12 (FIG. 9g). Tissue retractor head can then be deflated and device 10 pulled out of the body cavity through trocar port 70.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Ex-Vivo Retraction of Tissue Using a Cup-Shaped Retractor Head

A study was undertaken to evaluate the performance of a cup-shaped device prototype in retracting live tissue under a simulated body cavity environment.

Several prototypes were tested in order to evaluate the force needed to retract an intestinal segment and the force required for fixation of the retractor, as well as to identify optimal angles, shapes and depths of a retractor head.

Materials and Methods

Baskets (functioning as the retractor head) of different diameters (10-15 cm) and different materials—Plastic, rubber and carton were fabricated and tested on a freshly harvested pig intestines positioned within a bowl. The intestines were loaded into the baskets, pulled towards the side wall of the bowl and fixed against the wall by applying pressure on the crown of the basket. The pressure was then measured to determine the force needed to pull the intestines.

Figure 10:
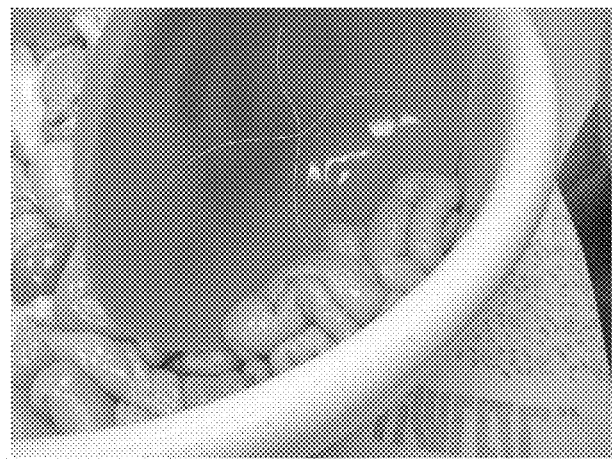
FIGS. 10-14 illustrate various developmental prototypes of the present device.

Pressure was applied to the center of ball-shaped basket while the rim of the basket was pressed against the sidewall of the bowel (concentrated pressure reflected by a dimple on the rubber ball face, FIG. 10). The force required to create the above mentioned dimple was measured (ball positioned on a weight scale).

Results

The results are summarized in Table 1 below.

TABLE 1

| Action | Pass/Failed | Remarks |
| --- | --- | --- |
| Preliminary impression on the cup concept | Pass | It can work. |
| Weight the amount of bowel in the cup | Failed | We were not able to weight it but the estimation is 1.5-2.5 kg. |
| moving intestines sideways | Pass | This weight is less relevant for side movement of intestines |
| Size | Pass | Cup size of 15 cm diameter seems to be large enough |
| cup Material | | Rubber seems adequate |

Conclusions

A cup 15 cm in diameter seems to be large enough for the retractor head. Using rubber for the retractor 'cup' resulted in less slippage of the intestines as compared to the plastic cup. In addition, soft material substantially reduces the chances of tissue trauma. Finally, these experiments showed that due to the positioning of the bowel within the retractor head, a symmetrical configuration is not necessary.

Example 2

Ex-Vivo Retraction of Tissue Using an Umbrella-Shaped Retractor Head

A study was undertaken to evaluate the performance of an umbrella-shaped device prototype in retracting live tissue under a simulated body cavity environment.

Figure 11:

Materials and Methods:

Two umbrella-shaped prototype having an inflatable rim 10 or 15 cm in diameter and a cone side cover were set over a rigid skeleton and tested with pig intestines positioned within a basket (FIG. 11).

The purpose of this study was to evaluate the efficacy of an umbrella-shaped prototype device in retracting tissue under simulated conditions. In particular these experiments were designed in order to test two sizes and diameters; weight the small bowel collected by the umbrella in order to evaluate the required force to retract an intestine segment; measure the force required for fixation of the retractor; and test different angles, shapes and depths of the retractor, as well as the need for retractor head symmetry.

Results

The results are summarized in Table 2 below.

TABLE 2

| Action | Pass/Failed | Remarks |
| --- | --- | --- |
| Preliminary impression on the Umbrella concept | Failed | Poor retraction capabilities and limited grasping capabilities |
| Side moving of the bowel | Failed | The umbrella shape has a poor ability to avoid movement of the intestine after fixation towards the abdominal wall |

TABLE 2-continued

| Action | Pass/Failed | Remarks |
| --- | --- | --- |
| Size | Pass | 10 cm seems to be more efficient, easier to perform maneuvers and a more robust fixation. 15 cm is too large and bulky |
| Material | | Rubber seems adequate |

Conclusions

A retractor head size of 10 cm diameter seems to be the adequate, while 15 cm in diameter seems too large. An umbrella shape retractor seems to have poor grasping/raking capabilities and does not hold the intestines following fixation.

Example 3

Ex-Vivo Retraction of Tissue Using a Hook-Shaped or Rake-Shaped Retractor Head

A study was undertaken to evaluate the performance of a hook or rake-shaped to device in retracting live tissue under a simulated body cavity environment.

Figure 12:
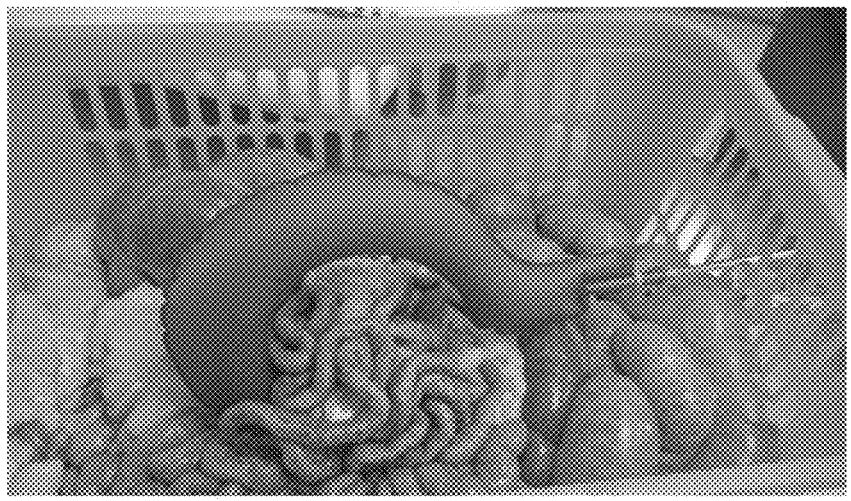
Figure 13:
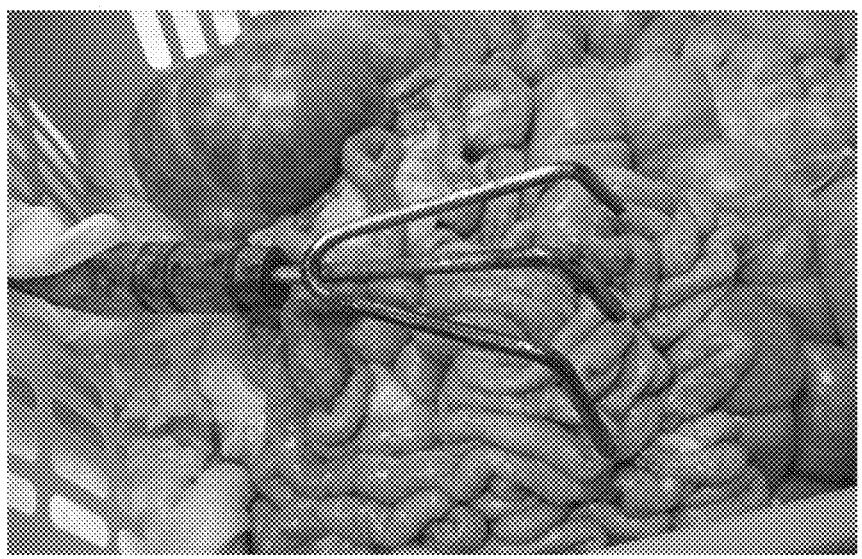
Figure 14:
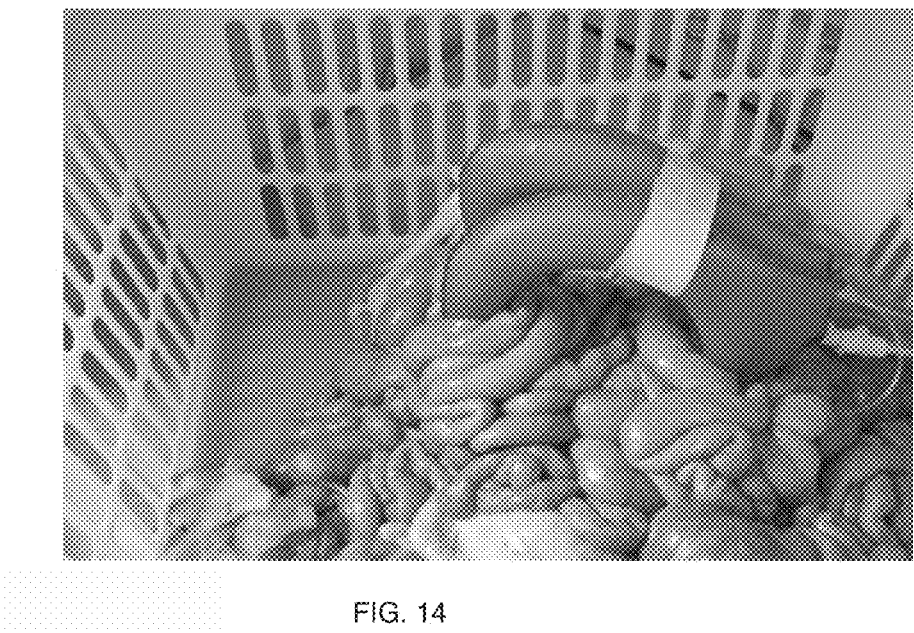

A balloon hook prototype (FIG. 12) and a rake device (FIG. 13) were tested for retraction of pig intestines positioned in a basket. The objectives of these experiments were to test grasping (sweeping) capabilities of each device; to evaluate the fixation of each device and its ability to contain the intestines over time; to measure the pressure (force) required for fixation of the retractor and to test different angles, shapes and depths of the retractor head.

Results

The results are presented in Tables 3 and 4 below.

TABLE 3

| hook | | |
| --- | --- | --- |
| Action | Pass/Failed | Remarks |
| Penetration into the intestine | Failed | Poor penetration capabilities into the intestine, requires functional support from other tools e.g. - grasper |
| Pulling/Grasping the | Pass | Once penetrate demonstrate very good pulling/grasping capabilities |
| Fixation | Pass | Very good fixation of the intestine - It didn't move at all for 15 minutes. As for 1st test - demonstrate ability to hold sufficient internal pressure for ~20 minutes without repeated pumping |
| Allowed tilting of the balloon root | Pass | Allowed tilting of the balloon root (the shaft-balloon connection) minimizes the parasite bending moment (mechanical moment) and adjusts itself to bring the pulling force aligned with the reaction force. That, in addition to the hook shape enabled to fix the intestine and overcome the peristaltic movement of it. |

TABLE 4

| rake | | |
| --- | --- | --- |
| Action | Pass/Failed | Remarks |
| Penetration among the intestine | Pass | Good penetration into the intestine |
| Pulling/Grasping the bowel | Pass | Very good grasping (sweeping) |

TABLE 4-continued rake

| Action | Pass/Failed | Remarks |
| --- | --- | --- |
| Fixation | Failed | Very poor fixation of the intestine due to its inability to adjust/compensate on inherent bending moment |

Conclusions

The inflated hook prototype demonstrated poor penetration into the tissue mass, but once engaged with the intestine it provided strong pulling capabilities and efficacious fixation. The rake demonstrated very good penetration and grasping capabilities but, as per tested configuration very poor fixation.

Example 4

Ex-Vivo Retraction of Tissue Using a Claw-Shaped Retractor Head

A double hook claw-shaped device was constructed by attaching 2 hook shaped balloons to a handle. The claw-shaped device was tested as described above in order to evaluate its performance in retracting pig intestines and compare it to the devices described above.

Results

The results of this study are presented in Table 5 below, performance was rated on a scale of 1-5, 5 being best.

TABLE 5 comparison

| | 100% soft, spaghetti ladle shaped balloon | Shielded spaghetti ladle shaped balloon | Double hook-100% soft | Rake - 3 fingers with an angle smaller than 90% | modified single hook |
| --- | --- | --- | --- | --- | --- |
| Penetration to the intestine | 1 | 1 | 1 | 5 | 1 |
| Sweeping | 1 | 4 | 5 hand assisted for penetration | 5 | 5 hand assisted for penetration |
| Fixation | NA-were not able to sweep | 4 | 5 | 5 | 5 |
| Release | 5 | 2-since it didn't have side walls | 5 | 5 | 5 |
| Ejection | 5 | NA | 5 | 5 | 5 |

Conclusions

A totally inflated double hook has a poor intestine mass penetration but once engaged with the intestine it provides strong pulling capabilities. Intestinal fixation with the double hook is satisfactory over 25 minutes. The rake device (described in Example 3) has good intestinal mass penetration and grasping capabilities. Decreasing the angle of the fingers to less than 90 degrees resulted in very good fixation. The umbrella/basket shaped device was not able to penetrate or sweep the intestines.

Example 5

Ex-Vivo Retraction of Pig Small Bowel Using a Rake-Shaped Retractor Head

Figure 15:
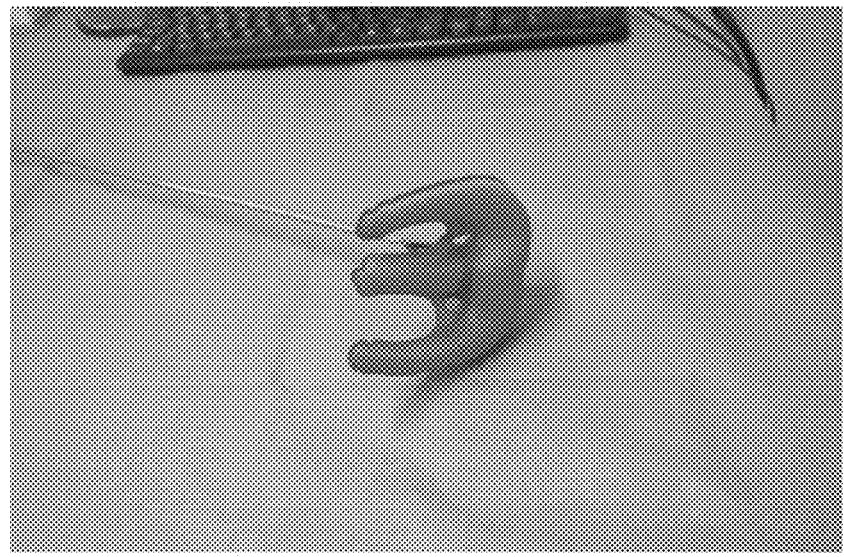
FIG. 15 illustrates a rake-shaped prototype of the present device.

A prototype of a fully Laparoscopic device with a rake-shaped balloon retractor head (FIG. 15) was tested using an ex-vivo set up which included a basket filled with freshly harvested pig small bowel simulating an abdominal cavity environment.

The purpose of this study was to evaluate the performance in retracting live tissue under simulated conditions. Parameters evaluated included:

(i) an ability to penetrate the intestinal mass (top down);
(ii) grasping and sweeping abilities;
(iii) an ability to maintain the intestines retracted over time;
(iv) an ability to withstand the pressure (force) required for fixation of the retractor;
(v) test different angles, shapes and depth of the retractor; and
(vi) sensing of peristaltic movement of the small bowel by fixing the device to a bed clamp for 30 minutes.

Procedure

The device included a 40 cm long shaft (having a diameter of 6 mm) attached to rake-shaped retractor head fabricated from polyethylene sheet and having the following dimensions when inflated: width—80 mm, height—80 mm and thickness (front to back)—20 mm. A strap attached to the shaft and looped around the middle finger of the retractor head enabled setting of the angle between the retractor head and shaft.

The device was tested in a low Anterior Resection procedure. The device was inserted into the abdominal cavity, the retractor head was inflated and the device was placed above the left colon (target organ) and was moved top down and inserted behind the intestines, thereby retracting and exposing the target organ. Two retractor angles were tested, 180 and 90 degrees.

Results

The results of this study are presented in Table 6 below. Performance was rated on a scale of 1-5, 5 being best.

TABLE 6

| | Lap device with Improved Balloon rake with a strap |
| --- | --- |
| Penetration to the intestine | 4 |
| Sweeping | 4 |
| Fixation | 4 |
| Release | 4 |

Figure 16:
FIG. 16 illustrates a bench testing setup including a basket containing pig bowels used for simulating an abdominal cavity surgical space.

The rake-shaped retractor head demonstrated mechanical stability which enabled effective retraction and sweeping of the intestine (FIG. 16). Configuring the retractor head such that the finger-like extension angle inward (less than 90°) greatly improves retraction and sweeping. Penetration was most efficient when the retractor head was set at 90° while extraction was facilitated by release of the strap and linearization)(180° of the retractor head. Small bowel fixation of over 20 minutes was achieved using the present device.

This study demonstrated that the rake-shaped retractor head of the present invention can effectively penetrate, fixate and sweep small bowel tissue while also being easily releasable therefrom.

Example 6

In-Vivo Testing of a Rake-Shaped Prototype—Pig 1

Two rake-shaped device prototypes similar in design to that described in Example 5 were tested for penetration, retraction and sweeping of intestines in a live female pig.

A first prototype included finger-like extension 7 cm in length while the second prototype included finger-like extension 3 cm in length.

The purpose of this study was to evaluate the performance in retracting live tissue under in-vivo conditions.

Parameters evaluated included:
(i) an ability to penetrate the intestinal mass (top down);
(ii) grasping and sweeping abilities;
(iii) an ability to maintain the intestines retracted over time;
(iv) an ability to withstand the pressure (force) required for fixation of the retractor;
(v) test different angles, shapes and depth of the retractor;
(vi) sensing of peristaltic movement of the small bowel;
(vii) fix the device against the abdominal wall for 30 minutes; and
(vii) introduce the device through a 10 mm trocar.

Procedure

The device prototypes were introduced through the 10 mm trocar and the balloon forming the retractor head was inflated via a 60 ml syringe. The retractor head was maneuvered via the handle and positioned above the intestines. With the retractor head set at a 90 degree angle, the finger-like extensions were forced between the folded intestinal segments. The intestines were retracted by pulling the retractor head towards the internal abdominal wall cavity with the intestines positioned against the finger-like extensions. Retraction was held for 30 minutes, following which the retractor head was deflated and the device removed through the 10 mm trocar.

Results

Prototype with 7 cm Fingers

Penetration of bowels with the device having the 7 cm long fingers proved difficult but once penetrated, grasping was effective. Fixation for 30 minutes with the device handle fixed to a bed clamp was achieved and extraction of the device following deflation of the retractor head was easily achieved.

Prototype with 3 cm Fingers

Penetration of bowels with the device having the 3 cm long fingers was easy; once penetrated, grasping and sweeping of bowls was effected with ease. Fixation for 30 minutes with the device handle fixed to a bed clamp was achieved and extraction of the device following deflation of the retractor head was easily achieved.

Conclusions

The device with 3 cm fingers was more effective in penetrating the intestine (top down). Both prototypes demonstrated the mechanical stability required for sweeping the intestines. A penetrating mode of 90° and an extracting mode of 180° proved optimal. Fixation of the intestines using a bed clamp was achieved for over 30 minutes with no visible tissue damage to the intestines; extraction of the device through the 10 mm trocar was easily achieved.

Example 7

In-Vivo Testing of a Rake-Shaped Prototype—Pig 2

Figure 17:
FIG. 17 illustrates a rake-shaped prototype of the present device which includes side extensions.

Two rake-shape prototypes having 2 cm fingers, one with additional side extensions (FIG. 17) were tested as described in Example 6.

The purpose of this study was to evaluate the performance in retracting live tissue under in-vivo conditions.

Parameters evaluated included:
(i) an ability to penetrate the intestinal mass (top down);
(ii) grasping and sweeping abilities;
(iii) an ability to maintain the intestines retracted over time;
(iv) an ability to withstand the pressure (force) required for fixation of the retractor;
(v) test different angles, shapes and depth of the retractor;
(vi) sensing of peristaltic movement of the small bowel;
(vii) fix the device against the abdominal wall for 30 minutes; and
(vii) introduce the device through a 10 mm trocar.

Results

Prototype with 2 cm Fingers:

The short fingers allowed easy top down penetration and efficient sweeping of the intestines. Fixation of the intestines via clamping of the device handle to a bed clamp was achieved for over 30 minutes without the intestines collapsing back. Extraction of the device (with deflated retractor head) through the 10 mm trocar was easily achieved.

Figure 18A:
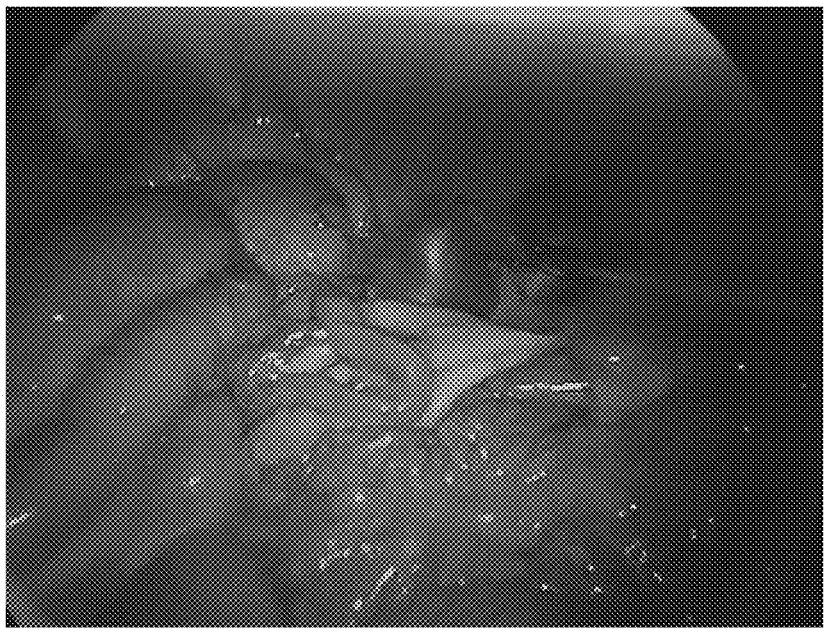
FIGS. 18A-B are endoscopic camera images showing tissue retraction using the rake-shaped prototype constructed in accordance with the teachings of the present invention.
Figure 18B:
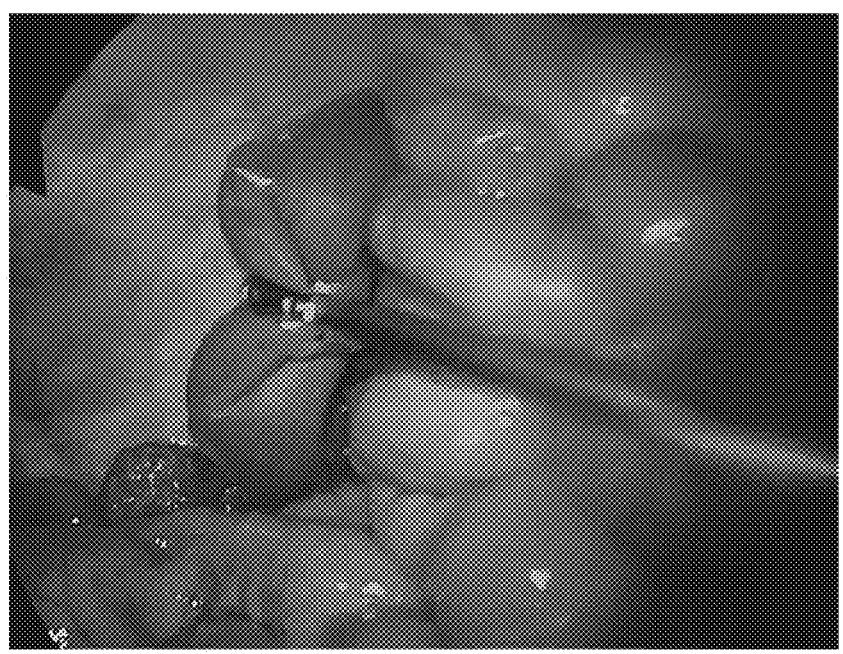

FIGS. 18a-b are images captured from the endoscopic camera used during the in-vivo procedure. These images clearly show that the 2 cm fingers of the rake-shaped-prototype can easily penetrate the intestinal folds (FIG. 18a) and retract the intestinal mass away from the surgical space (FIG. 18b).

Prototype with 2 cm Fingers and Side Extensions:

The short fingers allowed easy top down penetration and efficient sweeping of the intestines. Fixation of the intestines via clamping of the device handle to a bed clamp was achieved for over 30 minutes without the intestines collapsing back. Extraction of the device (with deflated retractor head) through the 10 mm trocar was easily achieved. The side fingers further facilitated capturing of the intestines, however, they hindered release of the intestines from the retractor head.

Conclusions

The 2 cm fingers were effective in penetrating and grasping the bowls, however, the side fingers, while facilitating grasping hindered release of the intestines from the retractor head. Both prototypes demonstrated the mechanical stability required for sweeping the intestines. A penetrating mode of 90° and an extracting mode of 180° proved optimal. Fixation of the intestines using a bed clamp was achieved for over 30 minutes with no intestines collapsing back and extraction through the 10 mm trocar was easily achieved.

Example 8

In-Vivo Testing of a Rake-Shaped Prototype—Pig 2

Two prototypes which included the handle of FIG. 7j and the rake-shaped tissue retractor head of FIG. 7c were tested in a pig. The two prototypes were identical except for the head release mechanism, one included a release button and the other required cutting of the string controlling the angle of tissue retractor head (54 in FIG. 7*c*).

The purpose of this study was to evaluate device performance in retracting live tissue. Experiments were conducted to evaluate the deployment, retraction and sizing required from the device.

The test objectives were as follows:
(i) ability to penetrate the intestine (top down);
(ii) ability to grasp and sweep intestines;
(iii) evaluate the intestinal fixation capabilities of the device over time;
(iv) to demonstrate the ability of the device to withstand the pressure (force) required for fixation of tissue and device;
(v) to feel (through the device) the peristaltic movement of the small bowel
(vi) delivery through a trocar 10 mm;
(vii) to test the release button and device extraction; and
(viii) to test cutting of the string with laparoscopic scissors and device extraction.

Results

The device easily penetrated the intestinal folds (top down) following inflation of the tissue retractor head. Sweeping was easily demonstrated and fixation to a bed clamp was maintained for over 30 minutes with no appreciable movement of the intestines. The device was rapidly deflated and removed through a 10 mm trocar. The same device was reused several times with similar results.

The device without the release button performed similarly, cutting the string with laparoscopic scissors enabled easy and fast removal of the device.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A tissue retractor device comprising:
a handle comprising a shaft and a user engaging portion;
said shaft attached to an inflatable tissue retractor head being configured such that when inflated with a fluid, said tissue retractor head includes at least one extension sized and configured for enabling said tissue retractor head to hook over tissue thereby enabling retraction and/or containment of said tissue within a body cavity; and
a strap interconnecting a region of said tissue retractor head to said handle for holding said head with respect to said handle such that a tissue receiving region is defined between said head and handle; said strap being wrapped around said at least one extension such that it passes from a first side of said at least one extension that faces said tissue receiving region, around an external side of said at least one extension, and back into said first side, said strap extending externally to said shaft of said handle at least along a portion of a length of said shaft such that a portion of said strap is spaced apart from said shaft when said head is angulated with respect to said shaft.

2. The tissue retractor of claim 1, wherein said handle includes a mechanism for angling a portion of said tissue retractor head with respect to said handle using said strap, during or following inflation of said tissue retractor head.

3. The tissue retractor of claim 2, wherein said strap is configured to maintain an angulation of about 90 degrees between said tissue retractor head and said handle.

4. The tissue retractor of claim 1, wherein said strap is attached to said handle via a hook mechanism.

5. The tissue retractor of claim 4, wherein said hook mechanism is attached to a push/pull wire controllable from said user engaging portion of said handle.

6. The tissue retractor of claim 1, wherein said tissue retractor head is deliverable through a laparoscopic port when in a deflated state.

7. The tissue retractor of claim 1, wherein said at least one extension is configured as a prong or hook.

8. The tissue retractor of claim 1, wherein said tissue retractor head is configured as a rake, a claw, or a hook.

9. The tissue retractor head of claim 1, wherein said tissue retractor head is fabricated as a two dimensional flat structure capable of being inflated to a three dimensional structure.

10. The tissue retractor of claim 1, wherein said handle includes a fluid conduit for allowing fluids to diffuse from an opening at said tissue retractor head to said handle.

11. The tissue retractor of claim 1, wherein said strap extends across a tissue receiving region defined between said tissue retractor head and said handle.

12. A method of retracting a tissue or organ comprising:
(a) positioning a tissue retractor device including a handle attached to an inflatable tissue retractor head within a body cavity;
(b) at least partially inflating said tissue retractor head in a position over the tissue or organ;
(c) setting a position of said tissue retractor head relative to said handle using a strap interconnecting a region of said tissue retractor head to said handle, said strap being wrapped around an at least one extension of said tissue retractor head such that it passes from a first side of said at least one extension that faces a tissue receiving region, around an external side of said at least one extension, and back into said first side, said strap extending externally to said shaft of said handle at least along a portion of a length of said shaft such that a portion of said strap is spaced apart from said shaft when said head is angulated with respect to said shaft; and
(d) using said tissue retractor device to retract the tissue or organ.

13. The method of claim 12, further comprising additionally inflating said tissue retractor head following (c) to thereby grasp the tissue or organ.

14. The method of claim 12, further comprising (e), partially deflating said tissue retractor head.

15. The method of claim 12, further comprising mechanically fixating said tissue retractor head in a predetermined position following (c).

16. The method of claim 12, further comprising using said tissue retractor device to trap the tissue or organ.

* * * * *